US012788891B2

(12) United States Patent
Nicholas et al.

(10) Patent No.: US 12,788,891 B2
(45) Date of Patent: Nov. 10, 2026

(54) AUTO-INJECTOR WITH ANTI-ROLL FEATURES

(71) Applicant: Regeneron Pharmaceuticals, Inc., Tarrytown, NY (US)

(72) Inventors: Courtney Nicholas, Fairfax, VA (US); Scott Barton, Clifton Park, NY (US); Bart E. Burgess, Bernville, PA (US); Alexei Goraltchouk, Cambridge, MA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 17/951,801

(22) Filed: Sep. 23, 2022

(65) Prior Publication Data

US 2023/0020306 A1 Jan. 19, 2023

Related U.S. Application Data

(63) Continuation of application No. 16/626,669, filed as application No. PCT/US2018/040282 on Jun. 29, 2018, now Pat. No. 11,484,654.

(Continued)

(51) Int. Cl.
*A61M 5/32* (2006.01)
*A61M 5/31* (2006.01)

(52) U.S. Cl.
CPC ........ *A61M 5/3129* (2013.01); *A61M 5/3202* (2013.01); *A61M 2205/19* (2013.01); *A61M 2205/582* (2013.01); *A61M 2205/583* (2013.01)

(58) Field of Classification Search
CPC ...... A61M 2205/582; A61M 2205/583; A61M 5/3202
See application file for complete search history.

(56) References Cited

U.S. PATENT DOCUMENTS

| | | | |
|---|---|---|---|
| 4,046,145 A | 9/1977 | Choksi et al. |
| 4,840,185 A | 6/1989 | Hernandez |

(Continued)

FOREIGN PATENT DOCUMENTS

| | | |
|---|---|---|
| AU | 2007269791 B2 | 1/2008 |
| CN | 101282752 A | 10/2008 |

(Continued)

OTHER PUBLICATIONS

U.S. Appl. No. 29/655,109, filed Jun. 29, 2018.

(Continued)

*Primary Examiner* — Emily L Schmidt
(74) *Attorney, Agent, or Firm* — Bookoff McAndrews, PLLC

(57) ABSTRACT

The present disclosure relates to a therapeutic agent delivery device with anti-roll features. In one embodiment, a therapeutic agent delivery device may include a tubular body including a first end portion, a second end portion, and a lumen extending between the first end portion and the second portion. An outer surface of the tubular body includes a first opening in communication with the lumen. The outer surface of the tubular body further may include a ledge extending around a periphery of the first opening, and a portion of the ledge closest to the second end portion of the tubular body may be shaped as an arrowhead. The therapeutic agent delivery device also may include a cap configured to engage the second end portion of the tubular body, wherein the cap may include a central longitudinal axis, a first end having a first cross-sectional dimension, and a second end having a second cross-sectional dimension larger than the first cross-sectional dimension. The cap may further include a curved sidewall extending radially outward from the first end to the second end, and the curved sidewall may include a protrusion.

20 Claims, 15 Drawing Sheets

Related U.S. Application Data

(60) Provisional application No. 62/527,408, filed on Jun. 30, 2017.

(56) References Cited

U.S. PATENT DOCUMENTS

| | | | |
|---|---|---|---|
| 4,900,309 | A | 2/1990 | Netherton et al. |
| 4,986,817 | A | 1/1991 | Code |
| 5,000,603 | A | 3/1991 | Isoda |
| 5,147,328 | A | 9/1992 | Dragosits et al. |
| 5,336,197 | A | 8/1994 | Kuracina et al. |
| 5,509,903 | A | 4/1996 | Grendahl et al. |
| 5,519,931 | A | 5/1996 | Reich |
| 5,554,127 | A | 9/1996 | Crouther et al. |
| 5,554,133 | A | 9/1996 | Haffner et al. |
| 5,716,346 | A | 2/1998 | Farris |
| 5,843,036 | A | 12/1998 | Olive et al. |
| 5,897,266 | A | 4/1999 | Robert |
| 5,997,513 | A | 12/1999 | Smith et al. |
| D426,299 | S | 6/2000 | Bydlon et al. |
| D428,651 | S | 7/2000 | Andersson et al. |
| 6,206,855 | B1 | 3/2001 | Kunkel et al. |
| D447,799 | S | 9/2001 | Jun |
| D460,552 | S | 7/2002 | Niermann et al. |
| D462,760 | S | 9/2002 | Ahlgrim et al. |
| D479,599 | S | 9/2003 | Bainton |
| D479,601 | S | 9/2003 | Tyce |
| D479,602 | S | 9/2003 | Bainton |
| D479,603 | S | 9/2003 | Tyce |
| D479,747 | S | 9/2003 | Bainton |
| D479,748 | S | 9/2003 | Tyce |
| D481,120 | S | 10/2003 | Hawley et al. |
| D488,864 | S | 4/2004 | Fago et al. |
| D490,149 | S | 5/2004 | Hawley et al. |
| D490,150 | S | 5/2004 | Hawley et al. |
| D490,151 | S | 5/2004 | Hawley et al. |
| D492,027 | S | 6/2004 | Tyce et al. |
| D492,405 | S | 6/2004 | Bainton |
| D493,526 | S | 7/2004 | Hwang |
| D503,797 | S | 4/2005 | Tyce |
| 7,189,217 | B2 | 3/2007 | Chang et al. |
| 7,307,265 | B2 | 12/2007 | Polsinelli et al. |
| D561,894 | S | 2/2008 | Hudson |
| 7,338,474 | B2 | 3/2008 | Kirk |
| 7,414,254 | B2 | 8/2008 | Polsinelli et al. |
| D581,047 | S | 11/2008 | Koshidaka |
| 7,449,012 | B2 | 11/2008 | Young et al. |
| D596,289 | S | 7/2009 | Kawamura |
| D598,539 | S | 8/2009 | Tyce |
| D599,008 | S | 8/2009 | Tyce |
| D599,009 | S | 8/2009 | Tyce |
| D599,010 | S | 8/2009 | Tyce |
| D599,011 | S | 8/2009 | Tyce |
| D600,794 | S | 9/2009 | Tyce |
| D600,795 | S | 9/2009 | Tyce |
| D606,649 | S | 12/2009 | Tyce |
| D606,650 | S | 12/2009 | Tyce |
| 7,635,348 | B2 | 12/2009 | Raven et al. |
| D608,442 | S | 1/2010 | Tyce |
| D610,251 | S | 2/2010 | Tyce |
| D610,252 | S | 2/2010 | Tyce |
| D610,676 | S | 2/2010 | Tyce |
| D612,486 | S | 3/2010 | Van der Stappen |
| 7,682,155 | B2 | 3/2010 | Raven et al. |
| D616,089 | S | 5/2010 | Van der Stappen |
| D619,247 | S | 7/2010 | Loe, Jr. |
| D621,929 | S | 8/2010 | Van der Stappen |
| D623,738 | S | 9/2010 | Van der Stappen |
| 7,794,432 | B2 | 9/2010 | Young et al. |
| D628,690 | S | 12/2010 | Galbraith |
| 7,846,136 | B2 | 12/2010 | Witowski |
| 7,905,352 | B2 | 3/2011 | Wyrick |
| D641,077 | S | 7/2011 | Sanders et al. |
| D651,305 | S | 12/2011 | Hawley et al. |
| 8,269,201 | B2 | 9/2012 | Fago et al. |
| D671,638 | S | 11/2012 | Young et al. |
| D676,957 | S | 2/2013 | Schneider et al. |
| 8,376,998 | B2 | 2/2013 | Daily et al. |
| D677,380 | S | 3/2013 | Julian et al. |
| D687,543 | S | 8/2013 | Pala et al. |
| D688,790 | S | 8/2013 | Guarraia et al. |
| D688,791 | S | 8/2013 | Guarraia et al. |
| D688,793 | S | 8/2013 | Guarraia et al. |
| D690,416 | S | 9/2013 | Cappello et al. |
| 8,529,510 | B2 | 9/2013 | Giambattista et al. |
| D692,129 | S | 10/2013 | Dubuc et al. |
| 8,591,463 | B1 | 11/2013 | Cowe |
| D694,879 | S | 12/2013 | Julian et al. |
| D695,892 | S | 12/2013 | Cappello et al. |
| D696,397 | S | 12/2013 | Guarraia et al. |
| D696,771 | S | 12/2013 | Schneider et al. |
| D696,773 | S | 12/2013 | Schneider et al. |
| D696,774 | S | 12/2013 | Guarraia et al. |
| D696,775 | S | 12/2013 | Guarraia et al. |
| D697,205 | S | 1/2014 | Schneider et al. |
| D703,314 | S | 4/2014 | Schneider et al. |
| D707,351 | S | 6/2014 | Kunze |
| D707,352 | S | 6/2014 | Liu et al. |
| D708,317 | S | 7/2014 | Schneider et al. |
| D710,498 | S | 8/2014 | Koshidaka |
| 8,801,679 | B2 | 8/2014 | Iio et al. |
| 8,821,451 | B2 | 9/2014 | Daniel |
| D714,932 | S | 10/2014 | Hall et al. |
| D715,422 | S | 10/2014 | Hall et al. |
| D716,442 | S | 10/2014 | Magome et al. |
| 8,864,718 | B2 | 10/2014 | Karlsen et al. |
| 8,870,827 | B2 | 10/2014 | Young et al. |
| D717,428 | S | 11/2014 | Sendatzki et al. |
| D717,940 | S | 11/2014 | Magome et al. |
| 8,888,713 | B2 | 11/2014 | Crawford et al. |
| D728,782 | S | 5/2015 | Dubuc et al. |
| 9,022,982 | B2 | 5/2015 | Karlsson et al. |
| D733,869 | S | 7/2015 | Ratjen |
| 9,078,973 | B2 | 7/2015 | Harms et al. |
| 9,132,236 | B2 | 9/2015 | Karlsson et al. |
| D740,937 | S | 10/2015 | Schneider et al. |
| 9,199,038 | B2 | 12/2015 | Daniel |
| 9,216,251 | B2 | 12/2015 | Daniel |
| 9,220,841 | B2 | 12/2015 | Daniel |
| 9,220,847 | B2 | 12/2015 | Holmqvist et al. |
| D748,253 | S | 1/2016 | Ratjen et al. |
| 9,247,899 | B2 | 2/2016 | Shaw et al. |
| D752,211 | S | 3/2016 | Sanders et al. |
| D755,369 | S | 5/2016 | Sanders et al. |
| D755,370 | S | 5/2016 | Riess et al. |
| D757,254 | S | 5/2016 | Wohlfahrt et al. |
| D757,255 | S | 5/2016 | Wohlfahrt et al. |
| D758,567 | S | 6/2016 | Wohlfahrt et al. |
| D758,568 | S | 6/2016 | Wohlfahrt et al. |
| D758,569 | S | 6/2016 | Wohlfahrt et al. |
| D764,657 | S | 8/2016 | Bokelman et al. |
| D770,038 | S | 10/2016 | Ahlgrim et al. |
| 9,468,722 | B2 | 10/2016 | Olson |
| D770,610 | S | 11/2016 | Saussaye et al. |
| D773,039 | S | 11/2016 | Sanders et al. |
| D773,648 | S | 12/2016 | Wohlfahrt et al. |
| D774,641 | S | 12/2016 | Miggels et al. |
| D777,907 | S | 1/2017 | Amend Kwasnik et al. |
| D777,912 | S | 1/2017 | Wohlfahrt et al. |
| 9,566,380 | B1 | 2/2017 | Tcholakian |
| D780,909 | S | 3/2017 | Burkett et al. |
| 9,586,010 | B2 | 3/2017 | Mesa et al. |
| 9,604,004 | B2 | 3/2017 | Jakobsen |
| D783,816 | S | 4/2017 | Wohlfahrt et al. |
| D785,784 | S | 5/2017 | Jones et al. |
| D787,666 | S | 5/2017 | Ohashi |
| 9,662,452 | B2 | 5/2017 | Daniel |
| D793,547 | S | 8/2017 | Burkett et al. |
| D794,178 | S | 8/2017 | Daniel et al. |
| D794,777 | S | 8/2017 | Daniel et al. |
| D800,897 | S | 10/2017 | Aneas |
| 9,808,580 | B2 | 11/2017 | Elmen |
| 9,867,940 | B2 | 1/2018 | Holmqvist et al. |
| D810,282 | S | 2/2018 | Ratjen |
| D814,022 | S | 3/2018 | Boyaval et al. |

(56) References Cited

U.S. PATENT DOCUMENTS

| | | | | |
|---|---|---|---|---|
| 9,931,469 | B2 | 4/2018 | Shain et al. | |
| 9,931,470 | B2 | 4/2018 | Kumar et al. | |
| D818,587 | S | 5/2018 | Shang et al. | |
| 9,962,490 | B2 | 5/2018 | Karlsson et al. | |
| 9,981,087 | B2 | 5/2018 | Shang et al. | |
| D822,198 | S | 7/2018 | Stonecipher et al. | |
| D827,127 | S | 8/2018 | Donnelly | |
| D830,539 | S | 10/2018 | Boyaval et al. | |
| 10,092,704 | B2 | 10/2018 | Daniel | |
| 10,098,910 | B2 | 10/2018 | Shanler et al. | |
| D834,706 | S | 11/2018 | Daniel et al. | |
| D834,707 | S | 11/2018 | Daniel et al. | |
| 10,130,774 | B2 | 11/2018 | Daniel | |
| 10,149,945 | B2 | 12/2018 | Moser et al. | |
| 10,188,798 | B2 | 1/2019 | Giambattista et al. | |
| D892,311 | S | 8/2020 | Nicholas et al. | |
| D898,191 | S | 10/2020 | Nicholas et al. | |
| 2003/0026642 | A1 | 2/2003 | Schwartzman | |
| 2004/0116875 | A1 | 6/2004 | Fischer et al. | |
| 2005/0011911 | A1 | 1/2005 | Vaughan | |
| 2007/0039156 | A1 | 2/2007 | Reich | |
| 2007/0113861 | A1 | 5/2007 | Knudsen et al. | |
| 2007/0184717 | A1* | 8/2007 | Hamazaki ............. | A61M 39/20 439/607.01 |
| 2007/0239114 | A1* | 10/2007 | Edwards ............. | A61M 5/3204 604/131 |
| 2008/0009808 | A1 | 1/2008 | Berler | |
| 2008/0210225 | A1 | 9/2008 | Geiger | |
| 2008/0269692 | A1 | 10/2008 | James et al. | |
| 2008/0289984 | A1 | 11/2008 | Raven et al. | |
| 2008/0312604 | A1 | 12/2008 | Boesen | |
| 2010/0266326 | A1 | 10/2010 | Chuang | |
| 2010/0274198 | A1 | 10/2010 | Bechtold | |
| 2013/0030375 | A1 | 1/2013 | Daily et al. | |
| 2013/0041328 | A1 | 2/2013 | Daniel | |
| 2013/0041347 | A1 | 2/2013 | Daniel | |
| 2013/0079718 | A1* | 3/2013 | Shang ..................... | A61M 5/20 604/131 |
| 2013/0172818 | A1* | 7/2013 | Schraga ................. | A61B 5/153 604/110 |
| 2013/0281934 | A1 | 10/2013 | Wilmot et al. | |
| 2014/0330216 | A1 | 11/2014 | Weaver et al. | |
| 2014/0358037 | A1 | 12/2014 | Crawford et al. | |
| 2014/0364812 | A1 | 12/2014 | Lumme et al. | |
| 2015/0011944 | A1 | 1/2015 | Young et al. | |
| 2015/0032062 | A1* | 1/2015 | Jakob .................. | A61M 5/3202 604/198 |
| 2015/0045742 | A1 | 2/2015 | Cheung | |
| 2015/0051580 | A1 | 2/2015 | Shain et al. | |
| 2015/0065960 | A1 | 3/2015 | Osman | |
| 2015/0073383 | A1 | 3/2015 | Wilmot et al. | |
| 2015/0080807 | A1 | 3/2015 | Schneider et al. | |
| 2015/0352278 | A1 | 12/2015 | Morita et al. | |
| 2015/0374918 | A1 | 12/2015 | Kumar et al. | |
| 2016/0051760 | A1 | 2/2016 | Krusell et al. | |
| 2016/0051764 | A1 | 2/2016 | Dreier et al. | |
| 2016/0067407 | A1 | 3/2016 | Daniel | |
| 2016/0089498 | A1 | 3/2016 | Daniel | |
| 2016/0144132 | A1 | 5/2016 | Scanlon | |
| 2016/0158460 | A1 | 6/2016 | Mesa et al. | |
| 2016/0213845 | A1 | 7/2016 | Holmqvist | |
| 2016/0263327 | A1 | 9/2016 | Radmer et al. | |
| 2016/0279334 | A1 | 9/2016 | Daniel | |
| 2016/0296716 | A1 | 10/2016 | Cabiri et al. | |
| 2016/0317745 | A1 | 11/2016 | Kjeldsen et al. | |
| 2016/0375196 | A1 | 12/2016 | Wilmot et al. | |
| 2017/0119969 | A1 | 5/2017 | Mccullough et al. | |
| 2017/0157332 | A1* | 6/2017 | Nguyen .............. | A61M 5/3204 |
| 2017/0203041 | A1 | 7/2017 | Julian et al. | |
| 2017/0259008 | A1* | 9/2017 | Fourt .................. | A61M 5/3204 |
| 2017/0290742 | A1 | 10/2017 | Henninger et al. | |
| 2018/0133407 | A1* | 5/2018 | Kemp ................. | A61M 5/3204 |
| 2018/0154078 | A1 | 6/2018 | Mosebach et al. | |
| 2018/0185413 | A1 | 7/2018 | Shanler et al. | |
| 2018/0221581 | A1 | 8/2018 | Kumar et al. | |
| 2018/0303875 | A1 | 10/2018 | Shanler et al. | |
| 2018/0304067 | A1 | 10/2018 | Ryan | |
| 2018/0311442 | A1 | 11/2018 | Saussaye et al. | |
| 2018/0318514 | A1 | 11/2018 | Daniel | |
| 2018/0318526 | A1 | 11/2018 | Yang et al. | |
| 2018/0344929 | A1 | 12/2018 | Dittrich | |
| 2018/0344930 | A1 | 12/2018 | Karlsson et al. | |
| 2018/0353692 | A1 | 12/2018 | Saussaye et al. | |
| 2018/0361082 | A1 | 12/2018 | Sall et al. | |
| 2019/0015595 | A1 | 1/2019 | Keitel | |
| 2019/0046565 | A1 | 2/2019 | Shanler et al. | |

FOREIGN PATENT DOCUMENTS

| | | | |
|---|---|---|---|
| CN | 101674772 | A | 3/2010 |
| EP | 2716318 | A1 | 4/2014 |
| EP | 004420388-0001 | | 10/2017 |
| EP | 004420388-0002 | | 10/2017 |
| EP | 004420388-0003 | | 10/2017 |
| EP | 004420388-0004 | | 10/2017 |
| EP | 004420388-0005 | | 10/2017 |
| EP | 004420388-0006 | | 10/2017 |
| EP | 004420388-0007 | | 10/2017 |
| EP | 004420388-0008 | | 10/2017 |
| EP | 004420388-0009 | | 10/2017 |
| EP | 004420388-0010 | | 10/2017 |
| EP | 004420388-0011 | | 10/2017 |
| FR | 3043562 | A1 | 5/2017 |
| GB | 2233607 | A | 1/1991 |
| JP | H10166785 | A | 6/1986 |
| JP | 2000025385 | A | 1/2000 |
| JP | 2003-290353 | A | 10/2003 |
| JP | 1401278 | | 11/2010 |
| JP | 1401279 | | 11/2010 |
| JP | 1401281 | | 11/2010 |
| JP | 1401282 | | 11/2010 |
| JP | 1401283 | | 11/2010 |
| JP | 2011-528247 | A | 11/2011 |
| JP | 2014506493 | A | 3/2014 |
| JP | 2014526368 | A | 10/2014 |
| JP | 2016511111 | A | 4/2016 |
| JP | 2016-73364 | A | 5/2016 |
| JP | 1587411 | | 10/2017 |
| WO | 2012073042 | A1 | 6/2012 |
| WO | 2015026737 | A1 | 2/2015 |
| WO | 2016/062807 | A1 | 4/2016 |
| WO | 2016/193350 | A1 | 12/2016 |
| WO | 2016193353 | A1 | 12/2016 |
| WO | 2017/004345 | A1 | 1/2017 |
| WO | 2017/081421 | A1 | 5/2017 |

OTHER PUBLICATIONS

International Search Report for PCT Application No. PCT/US2018/040282, mailed on Nov. 13, 2018, 13 pages.

SHL Medical Products Molly Auto Injectors (http://www.shl-group.com/Products_SHLMedical_AutoInjectors_Molly.html), last accessed Jul. 26, 2018.

Molly 2.25, SHL Group, https://pdf.medicalexpo.com/pdf/shl-group/molly-225-auto-injector-product-datasheet/118709-183270-_2.html, 2016.

EUIPO Design Gazette, 004420388-0001, HH29206315 (Oct. 25, 2017).

EUIPO Design Gazette, 004420388-0011, HH29206317 (Oct. 25, 2017).

International Bureau Design Gazette, DM/092744, HH29502547. (Sep. 6, 2016).

International Bureau Design Gazette, DM/098096, HH29513908 (Sep. 11, 2017).

* cited by examiner

AUTO-INJECTOR WITH ANTI-ROLL FEATURES

CROSS-REFERENCE TO RELATED APPLICATION(S)

This application is a continuation application under 37 CFR § 1.53(b) of U.S. Nonprovisional patent application Ser. No. 16/626,669, filed on Dec. 26, 2019, which is the U.S. National Stage Entry of International Application No. PCT/US2018/040282, filed Jun. 29, 2018, published as WO 2019/006296, which claims priority to U.S. Provisional Application No. 62/527,408, filed Jun. 30, 2017, the entireties of which are incorporated by reference herein.

INTRODUCTION

Various embodiments of the present disclosure relate to a therapeutic agent delivery device (e.g., an auto-injector or other injection device) having one or more anti-roll features configured to reduce and/or prevent rolling of the delivery device. The anti-roll features may be provided only on a body of the delivery device, only on a cap configured to removably engage the delivery device, or on both the body and the cap of the delivery device.

As illustrated in U.S. Pat. No. 8,529,510 B2, for example, injection devices may include a tubular housing susceptible to rolling across a surface when the device is placed on its side (e.g., when a longitudinal axis of the device is parallel or otherwise substantially parallel to the surface). Thus, there is a need for one or more anti-roll features designed to prevent rolling of the device.

Furthermore, injection devices have an injection end from which a needle may extend for penetration into a user. To prevent inadvertent needle injuries and/or damage to the needle, there is a need to readily communicate and/or otherwise indicate the injection end to the user. The injection device described in U.S. Design Pat. No. D677,380 is provided with an arrow pointing to the injection end of the depicted injection device. The provided arrow, however, is flush with the outer surface of the injection device and, thus, is difficult or impossible to perceive by, e.g., the visually-impaired. Moreover, rolling of the injection device described in the '380 patent is prohibited by providing the injection device with a generally rectangular cross-sectional configuration. However, providing the injection device with separate features for prohibiting rolling (e.g., the rectangular cross-section configuration) and indicating the injection end (e.g., a printed arrow) unduly complicates manufacturing and increases costs.

Thus, there is a need for an injection device anti-roll feature that also is configured to indicate the injection end to the user, regardless of whether the user is sighted or visually-impaired.

SUMMARY

According to one aspect of the disclosure, a therapeutic agent delivery device may include a tubular body including a first end portion, a second end portion, and a lumen extending between the first end portion and the second portion. An outer surface of the tubular body includes a first opening in communication with the lumen. The outer surface of the tubular body further may include a ledge extending around a periphery of the first opening, and a portion of the ledge closest to the second end portion of the tubular body may be shaped as an arrowhead. The therapeutic agent delivery device also may include a cap configured to engage the second end portion of the tubular body, wherein the cap may include a central longitudinal axis, a first end having a first cross-sectional dimension, and a second end having a second cross-sectional dimension larger than the first cross-sectional dimension. The cap may further include a sidewall extending radially outward from the first end to the second end, and the sidewall may include a protrusion.

Various embodiments of the therapeutic agent delivery device may include one or more of the following aspects: the therapeutic agent delivery device may be an auto-injector; the lumen of the therapeutic agent delivery device may be configured to receive a syringe therein, wherein the syringe may include a volume of the therapeutic agent, and wherein the first opening is configured to permit visualization of the volume of the therapeutic agent; when the cap of the therapeutic agent delivery device is not engaged with the tubular body, the ledge may be configured to restrict rolling of the tubular body; when the cap of the therapeutic agent delivery device is engaged with the tubular body, only the protrusion may be configured to restrict rolling of the therapeutic agent delivery device; the protrusion of the cap may include a plurality of protrusions, wherein each protrusion of the plurality of protrusions may be circumferentially spaced from an adjacent protrusion; the cap of the therapeutic agent delivery device may include a recess disposed between adjacent protrusions, wherein the protrusion includes a first end and a second end, wherein the first end of the protrusion is spaced from the central longitudinal axis of the cap by a first distance, and wherein the second end of the protrusion is spaced from the central longitudinal axis of the cap by a second distance greater than the first distance; and the outer surface of the tubular body of the therapeutic agent delivery device may further include a second opening disposed diametrically opposite to the first opening.

In another aspect, the present disclosure includes a therapeutic agent delivery device having a tubular body including a first end portion, a second end portion, and a central longitudinal axis, wherein an outer surface of the tubular body includes a geometric configuration extending away from the central longitudinal axis, a portion of the geometric configuration is shaped as an arrowhead, and the geometric configuration is configured to restrict rolling of the tubular body. The therapeutic agent delivery device further includes a cap configured to engage the second end portion of the tubular body, wherein the cap may include a first end including an opening in communication with an interior of the cap, a second end having an end wall, and a sidewall extending radially outward from the first end to the second end, and wherein the sidewall includes a protrusion configured to restrict rolling of the cap.

Various embodiments of the therapeutic agent delivery device may include one or more of the following aspects: the outer surface of the tubular body of the therapeutic agent delivery device may include a plurality of geometric configurations, wherein each geometric configuration may include a portion shaped as an arrowhead; the geometric configurations may be circumferentially spaced from one another on the outer surface of the tubular body, the outer surface of the tubular body includes a window, and wherein the geometric configuration surrounds a portion of the window; the window permits visualization of an interior of the tubular body; and the sidewall of the cap may include a plurality of protrusions circumferentially spaced from one another.

BRIEF DESCRIPTION OF THE DRAWINGS

The accompanying drawings, which are incorporated into and constitute a part of this specification, illustrate various exemplary embodiments and, together with the description, serve to explain the principles of the disclosed embodiments. The drawings show different aspects of the present disclosure and, where appropriate, reference numerals illustrating like structures, components, materials and/or elements in different figures are labeled similarly. It is understood that various combinations of the structures, components, and/or elements, other than those specifically shown, are contemplated and are within the scope of the present disclosure.

There are many inventions described and illustrated herein. The described inventions are neither limited to any single aspect nor embodiment thereof, nor to any combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein. Notably, an embodiment or implementation described herein as "exemplary" is not to be construed as preferred or advantageous, for example, over other embodiments or implementations; rather, it is intended reflect or indicate the embodiment(s) is/are "example" embodiment (s).

Figure 1A:
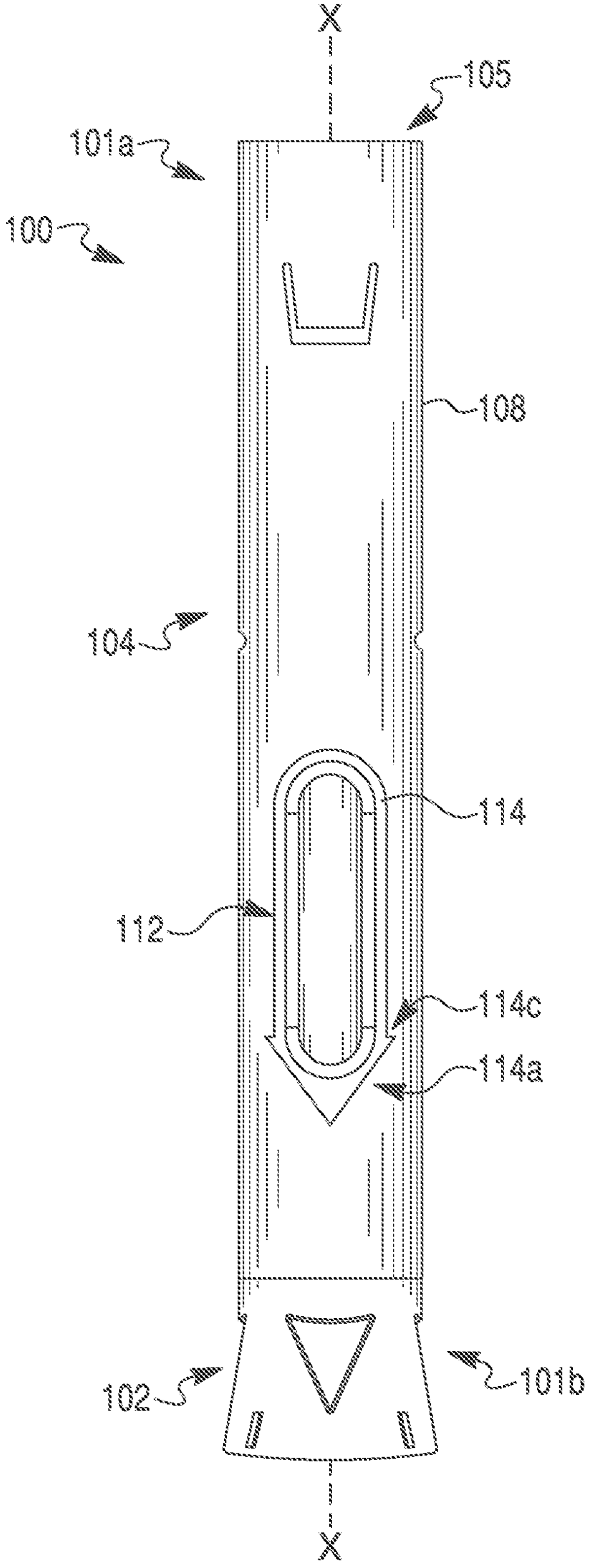
FIG. 1A provides a side view of an exemplary therapeutic agent delivery device, according to one embodiment of the present disclosure.

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." In addition, the terms "first," "second," and the like, herein do not denote any order, quantity, or importance, but rather are used to distinguish an element, a structure from another. Moreover, the terms "a" and "an" herein do not denote a limitation of quantity, but rather denote the presence of one or more of the referenced items.

The term "distal end," or any variation thereof, refers to the portion of the device farthest from a patient's injection or therapeutic agent delivery site during an injection operation. Conversely, the term "proximal end," or any variation thereof, refers to the portion of the device closest to a patient's injection or therapeutic agent delivery site during an injection operation. Further, as used herein, the terms "about," "substantially," and "approximately" generally mean +/−10% of the indicated value.

DETAILED DESCRIPTION

Embodiments of the present disclosure relate to a therapeutic agent delivery device (e.g., an auto-injector or other injection device) with anti-roll features on its tubular body and/or cap. Such features facilitate use of the auto-injector by providing predictability to the device's position. For example, anti-roll features on the described auto-injector may reduce the likelihood that the auto-injector will inadvertently roll off of a surface of, e.g., a table or a counter, or roll away from a user. In one embodiment, the outer surface of the housing of the auto-injector may include one or more raised portions or geometric configurations that reduce or otherwise prevent rolling of the housing. The raised portions or geometric configurations also may be configured to indicate to a user an injection end of the auto-injector (from which a needle may be extend into a user). In other embodiments, the auto-injector may include a cap configured to cover an injection end of the auto-injector. In such embodiments, the cap also may provided with anti-roll features. It will be understood by one of ordinary skill in the art that, while various utilitarian characteristics and features of auto-injectors are described herein, and several variations of those characteristics and features are described, those characteristics and features may be presented in a multitude of aesthetic ways on, in, or as a part of a device according to the present disclosure. In depicting one or a few visual variations on a characteristic or feature herein, the present disclosure is not intended to be limited by the depicted variations. Aspects of the present disclosure are described in greater detail below.

Figure 2A:
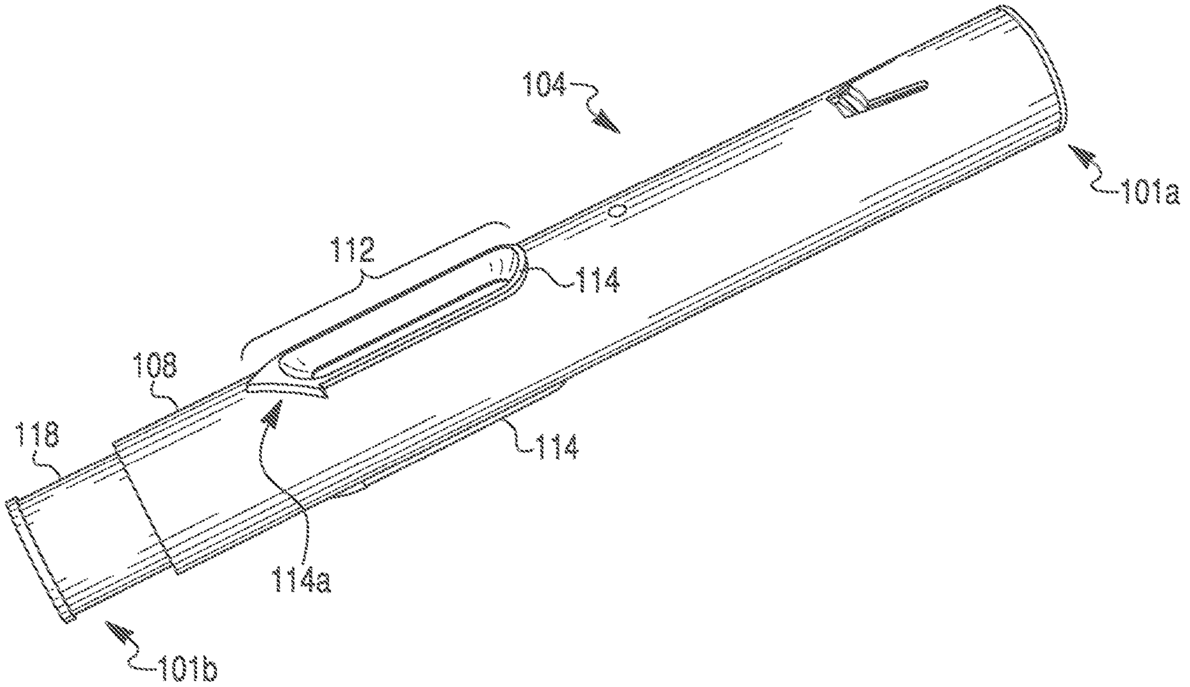
FIG. 2A provides a perspective view of a housing of the therapeutic agent delivery device of FIG. 1A.

As shown in FIG. 1A, an exemplary therapeutic agent delivery device 100 may include an injection device, including, but not limited to, an auto-injector. Delivery device 100 may include a distal end portion 101*a* and a proximal end portion 101*b*. Delivery device 100 may include an elongate housing 104 and a cap 102 configured to removably engage the proximal end of housing 104. Distal end portion 101*a* may include an opening into housing 104. Such an opening may be closed by a cap, as shown in FIG. 2A. The cap may have any suitable size or configuration. In some embodiments, the cap may be flush or substantially flush with distal end portion 101*a* of housing 104, so as to definitely communicate to a user that distal end portion 101*a* is not an injection end of delivery device 100. Housing 104 may include a generally circular cross-sectional configuration. In some embodiments, however, housing 104 may include any suitable cross-sectional configuration, including, but not limited to, rectangular, triangular, or oval-shaped. Housing 104 may include any suitable material, including, but not limited to, glass, plastic, metal, rubber, silicone, or a combination thereof. In some embodiments, housing 104 may be generally opaque. In other embodiments, however, housing 104 may include one or more transparent or translucent portions to permit visualization into housing 104. For example, as discussed in greater detail below, housing 104 may include one or more openings or windows to permit such visualization. In some embodiments, the windows may be covered by a transparent or translucent material such as, e.g., glass or plastic.

Housing 104 may include a lumen 105 and an outer surface 108. Outer surface 108 may include an opening or window (e.g., opening 112 shown in FIG. 1B) configured to permit visualization into housing 104, or permit visualization of contents within the lumen 105 (FIG. 2B) of housing 104. Though a single opening 112 is depicted in FIG. 1A, housing 104 may be provided with a greater number of openings 112, including, e.g., two openings, three openings, or four or more openings. In some embodiments, however, housing 104 may be provided without any openings. In embodiments having a plurality of openings 112, the openings 112 may be spaced circumferentially around outer surface 108. For example, two openings 112 may be positioned diametrically opposite to each other. Additionally, or alternatively, the openings 112 may be longitudinally spaced apart from one another on outer surface 108. For example, a first opening 112 and a second opening 112 may be positioned at generally the same radial position on outer surface 108, but longitudinally spaced along axis X-X. Moreover, opening 112 may include any suitable configuration. For example, openings 112 may be shaped as a circle, rectangle, triangle, pentagon, octagon, or an oval. As shown in FIG. 1A, e.g., opening 112 may include an elongate configuration. For example, a width of opening 112 may be approximately 7.5 mm and a length of opening may be approximately 31.9 mm. In some embodiments, the length of opening 112 may be much shorter than approximately 31.9 mm, e.g., when housing 104 is configured to receive a syringe 106 that is configured to hold less than 1 mL. The width of opening 112 may be constant or vary along its length. For example, a width of a proximal portion of opening 112 may be larger than a width of a distal portion of opening 112, thereby providing opening 112 with a generally hastate configuration. In some embodiments, sidewalls of opening 112 may taper away from one another.

In some embodiments, a proximal end of opening 112 may be configured to indicate an injection end to a user. For example, a proximalmost side of opening 112 may be configured to terminate in an apex "pointing" towards cap 102. Alternatively, a proximalmost side of opening 112 may be configured as an arrowhead pointing towards cap 102.

As alluded to above, outer surface 108 may include one or more anti-roll features configured to prevent or otherwise inhibit rolling of housing 104. For example, housing 104 may include one or more protrusions disposed about opening 112. As described in greater detail below, the anti-roll feature(s) may include a raised ledge 114 surrounding a portion or an entirety of the periphery of the opening 112, as shown FIGS. 1A-1C and 2A-2C, and described in greater detail below. Specifically, the present disclosure contemplates that ledge 114 may extend 100% percent around opening 112, less than 100% around opening 112, less than 75% around opening 112, less than 40% around opening 112, less than 30% around opening 112, or less than 20% around opening 112. Those of ordinary skill in the art will readily recognize that the described anti-roll features may be provided on outer surface 108 even if outer surface 108 does not include an opening 112. Even in embodiments where a plurality of openings 112 are provided on outer surface 108, one or more openings 112 may not include an associated ledge 114, or all openings 112 may include an associated ledge 114. Regardless, the present disclosure contemplates multiple ledges on outer surface 108. Further, outer surface 108 may include one or more geometric features configured to promote gripping by a user during handling. Such geometric features may include texturing, protrusions, recessed scallops, and/or low-strength heat activated adhesive material (e.g., a material configured to provide a temporary adhesive surface when activated by the heat of a user's hand).

Figure 1B:
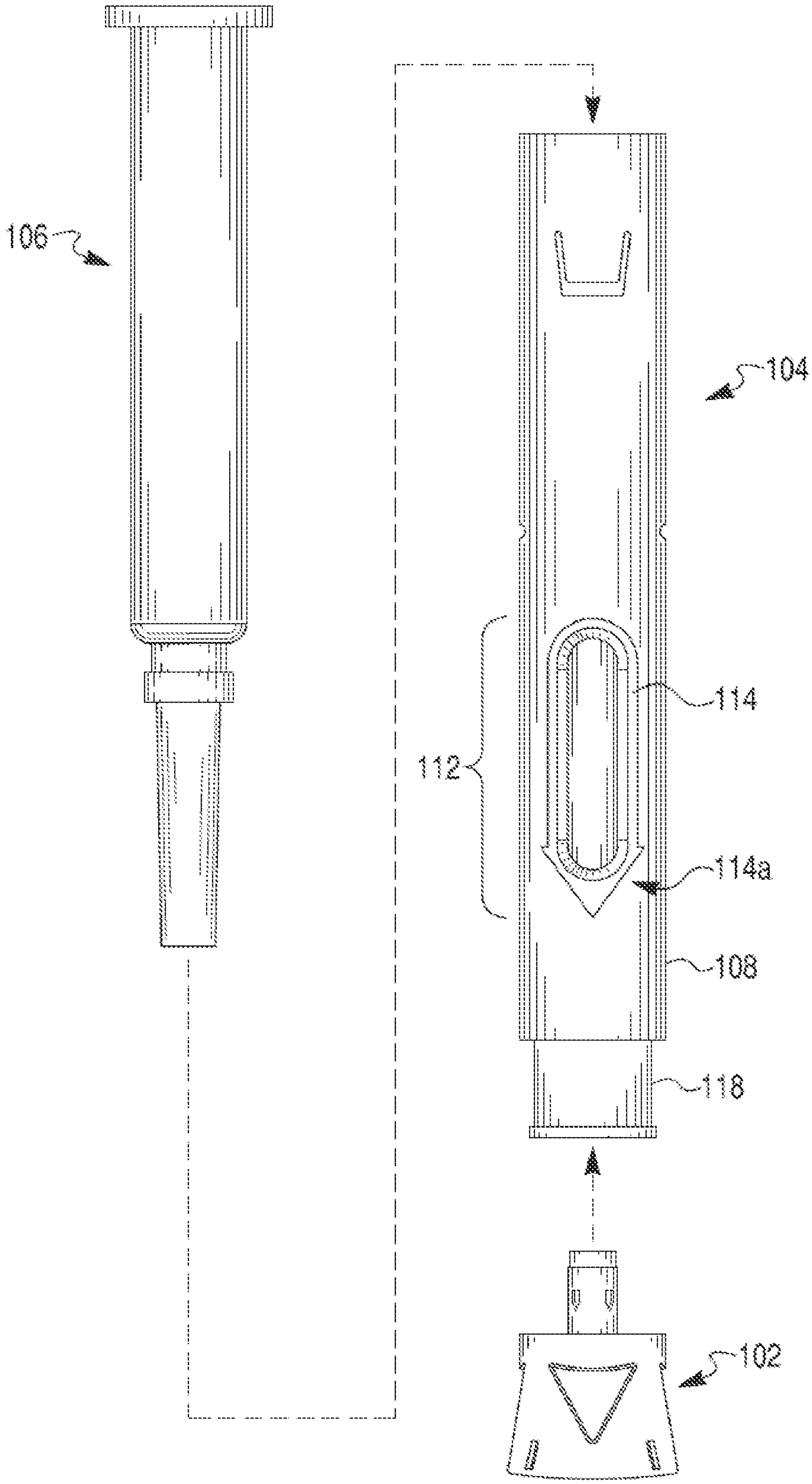
FIG. 1B provides an exploded view of the therapeutic agent delivery device of FIG. 1A.
Figure 1C:
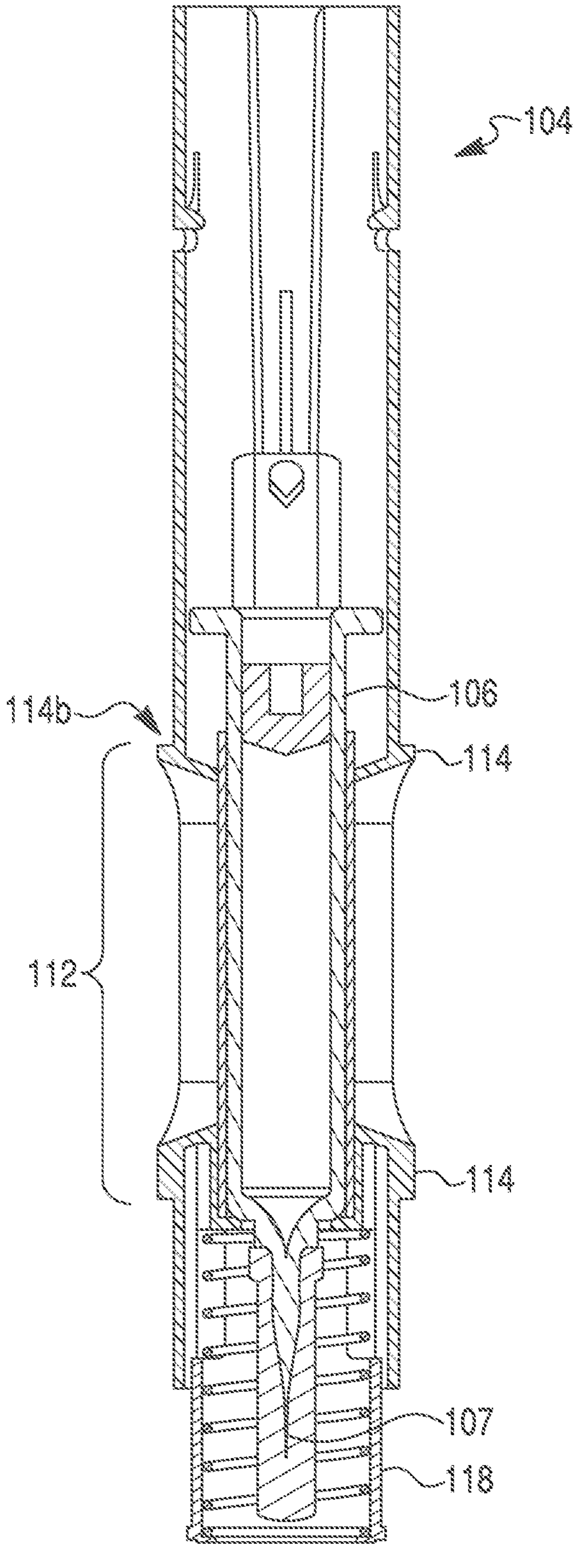
FIG. 1C provides a section view of the therapeutic agent delivery device of FIG. 1A taken along line X-X, where the device contains a syringe assembly and a power pack, according to one embodiment.
Figure 2B:
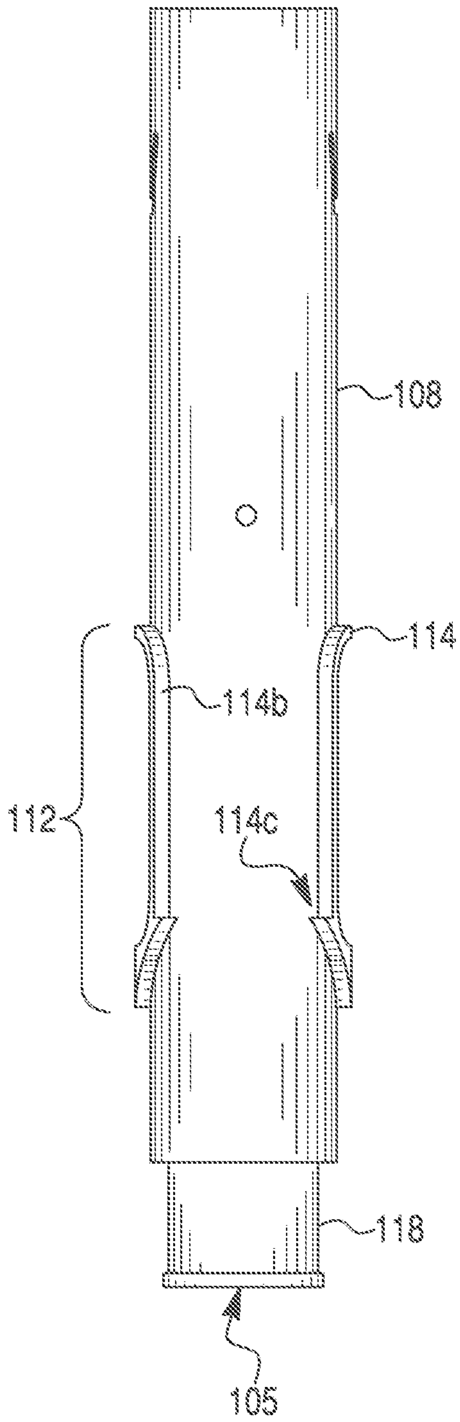
FIG. 2B provides a side view of the housing depicted in FIG. 2A, wherein the housing is rotated 90°. relative to the viewpoint shown in FIG. 1A.
Figure 2C:
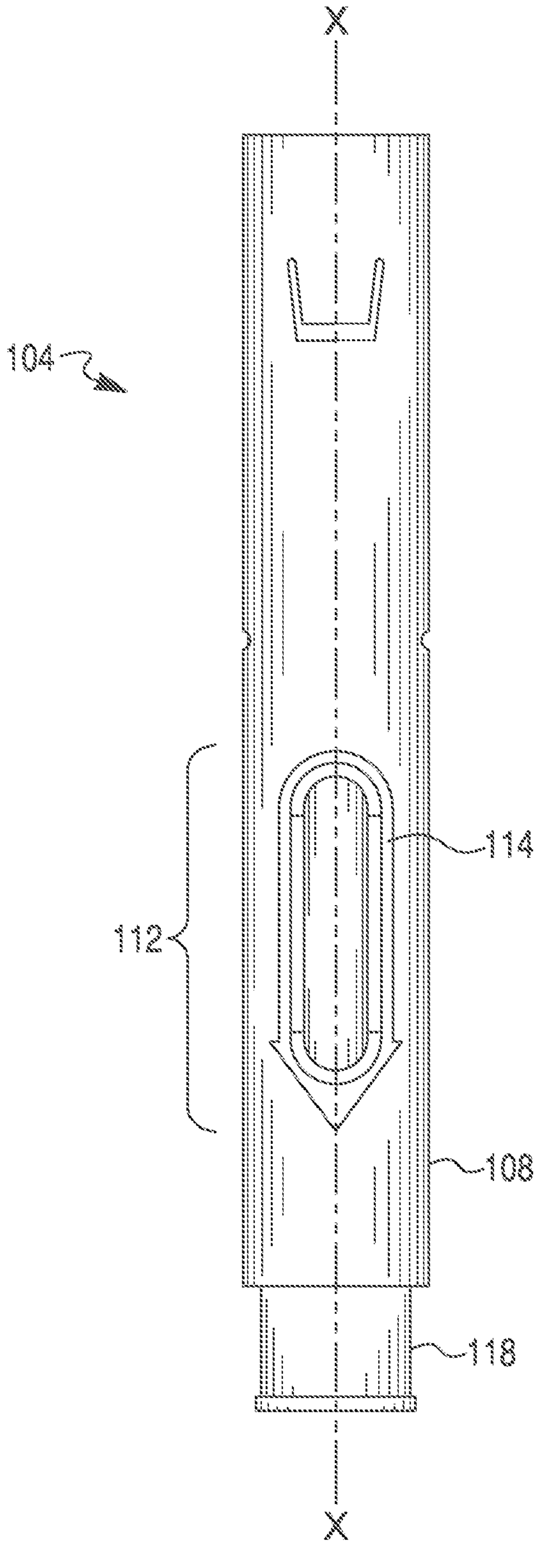
FIG. 2C provides another side view of the housing depicted in FIG. 2A, wherein the housing is rotated 90° relative to the viewpoint shown in FIG. 2B.

Ledge 114 may include any suitable configuration. For example, ledge 114 may include a generally rectangular cross-sectional configuration. In some embodiments, a radially outermost surface of ledge 114 (e.g., a surface of ledge 114 that is parallel with outer surface 108) may be curved to, e.g., promote comfort during handling. A sidewall (e.g., sidewall 114*b* shown in FIG. 1C) of ledge 114 may define a 90 degree angle with outer surface 108. In some embodiments, the angle defined by sidewall 114*b* may be greater or lesser than 90 degrees. In yet further embodiments, sidewall 114*b* may taper gradually away from outer surface 108. In embodiments where ledge 114 surrounds a substantial entirety of opening 112, ledge 114 may include a substantially uniform configuration (e.g., cross-sectional configuration). Alternatively, one or more portions of ledge 114 may include a configuration different than a remainder of ledge 114. For example, as shown in FIGS. 1A-1C, a proximal end portion 114*a* of ledge 114 may be configured to communicate a direction to a user. More specifically, proximal end portion 114*a* may include a proximally tapering configuration. For example, proximal end portion 114*a* may be shaped as an arrowhead, spear, sagittate, or hastate pointing toward proximal end 101*b*. In alternative embodiments, proximal end portion 114*a* may be shaped as a barb, a bolt, or a wedge. In yet further embodiments, proximal end portion 114*a* may include an elongate portion having a length dimension larger than a width dimension for some or all of the elongate portion. Though not depicted, one or more corners of distal end portion (e.g., corner 114*c* of the arrowhead illustrated in FIG. 1A) may be rounded.

Ledge 114 and housing 104 may be made in a one-piece configuration. For example, ledge 114 may be formed integrally with outer surface 108 during a molding process. Alternatively, ledge 114 may be affixed or otherwise secured to outer surface 108 during process subsequent to the formation of housing 104. For example, ledge 114 may be fabricated separately from the manufacture of housing 104 and adhered about opening 112 via a suitable adhesive compound or a welding process. In such embodiments, it is contemplated that ledge 114 may be "retro-fitted" to an outer surface of an already-manufactured housing of an injection device. Those of ordinary skill in the art will understand that ledge 114 may be manufactured by any suitable process, including, but not limited to, molding, 3D printing, and/or cutting.

In some embodiments, ledge 114 may include a constant height and/or width or may include varying heights and/or widths. For example, ledge 114 may include a serrated or corrugated profile. Specifically, adjacent portions of ledge 114 may be separated by outer surface 108.

Turning now to FIG. 1B, there is depicted an exploded view of delivery device 100 including cap 102, housing 104, and syringe 106 configured to be received within lumen 105 of housing 104. Syringe 106 may be configured to include a therapeutic agent, such as, e.g., a biologic or other formulation intended for delivery (via, e.g., needle 107 depicted in FIG. 1C) to (and/or by) a user of device 100. In some embodiments, syringe 106 may be configured to hold at least 1 mL of the therapeutic agent. In other embodiments, syringe 106 may be configured to hold a nominal volume of at least 1 mL, 1.5 mL, 2 mL, 2.25 mL, 3 mL, or 5 mL of the therapeutic agent. In other embodiments, syringe 106 may be configured to hold a nominal volume of less than 1 mL. Housing 104 also may include any suitable injection activation and/or propulsion mechanism, such as, e.g., a power pack for actuating needle 107 and/or delivering the therapeutic agent. Such an injection activation and/or propulsion mechanism may be disposed in any suitable location in device 100.

As alluded to above, opening 112 may be configured to permit a user of device 100 to visualize the contents of syringe 106. For example, the user may be able to recognize that device 100 has been used by determining that syringe 106 is empty or otherwise partially empty. Similarly, the user may be able to recognize that device 100 is unused by determining that syringe 106 is full (or substantially full) of therapeutic agent. Housing 104 may further include a needle cover 118, configured to, e.g., cover all or a portion of needle 107 of syringe 106 when syringe 106 is received within housing 104. In one embodiment, needle cover 118 may be retracted into housing 104, e.g., if force is exerted against the proximal end of needle cover 118 in the distal direction.

Turning now to FIGS. 1A, 1B, 3A-3E, 4A-4C, and 5A-5C there is depicted cap 102. As alluded to above, cap 102 may be configured to engage the proximal end of housing 104. With specific reference to FIGS. 3A-3E, 4A-4C, and 5A-5C, cap 102 may include a central longitudinal axis C-C. Cap 102 may include a distal end portion 130 and a proximal end portion 132. Distal end portion 130 may include a diameter smaller than a diameter of proximal end portion 132. Alternatively, though not shown, distal end portion 130 may include a diameter greater than a diameter of proximal end portion 132. Still further, distal end portion 130 and proximal end portion 132 may include substantially similar diameters. In some embodiments, distal end portion 130 may include an outer diameter substantially equal to an outer diameter of housing 104. In embodiments where proximal end portion 132 includes a diameter larger than the diameter of distal end portion 130, an outer diameter of proximal end portion 132 also may be larger than the outer diameter of housing 104.

Proximal end portion 132 may be defined by a proximal end face 132*a*. Proximal end face 132*a* may include a substantially flat configuration. Proximal end face 132*a* may be a substantially continuous wall configured to close a proximal end of cap 102. In this manner, the contemplated disclosure prevents use of the disclosed devices without removing cap 102. Cap 102 also may include a generally cylindrical skirt 134 depending from proximal end face 132*a*. In some embodiments, a circular groove 133 may be disposed between skirt 134 and proximal end face 132*a*. Skirt 134 may define an opening 135 at distal end 130 into an interior of cap 102. Opening 135 may be configured to receive needle cover 118 so that cap 102 may releasably engage housing 104.

Cap 102 may include a second skirt (not shown) disposed within opening 135, depending from an interior surface of proximal end face 132*a*, and arranged concentrically with skirt 134. The second skirt may include a diameter that is smaller than a diameter of skirt 134. Moreover, the second skirt may include a length that is smaller than a length of skirt 134. With renewed reference to FIGS. 3A, 4A, and 5A, cap 102 may include a cylindrical extension 143 extending from the second skirt and distally beyond skirt 134 and distal end portion 130 of cap 102. Cylindrical extension 143 may be disposed generally in the center of skirt 134. In one embodiment, cylindrical extension 143 may define a central lumen (not shown). The lumen may be configured to received a resilient material 144 therein. In some embodiments, the resilient material 144 may define a lumen 143*a* for receiving, e.g., a needle. Cylindrical extension 143 may include one or more selectively activated gripping features configured to retain resilient material 144 within lumen 143. Cylindrical extension 143 may be secured within the second skirt or may be fabricated together with cap 102 as a one-piece construction. An outer diameter of cylindrical extension 143 may be smaller than an inner diameter of the second skirt. Further, the second skirt may be configured to be received within a lumen of needle cover 118.

Cap 102 may be made of any suitable material, including, but not limited to, glass, plastic, metal, rubber, silicone, or a combination thereof. In some embodiments, cap 102 may be made of the same material as housing 104. In other embodiments, cap 102 may be made of at least one material different than the material of housing 104. Still further, cylindrical extension 143 may be made of a material different from a remainder of cap 102. For example, cap 102 may be made of plastic and cylindrical extension 143 may be made of metal.

Figure 3A:
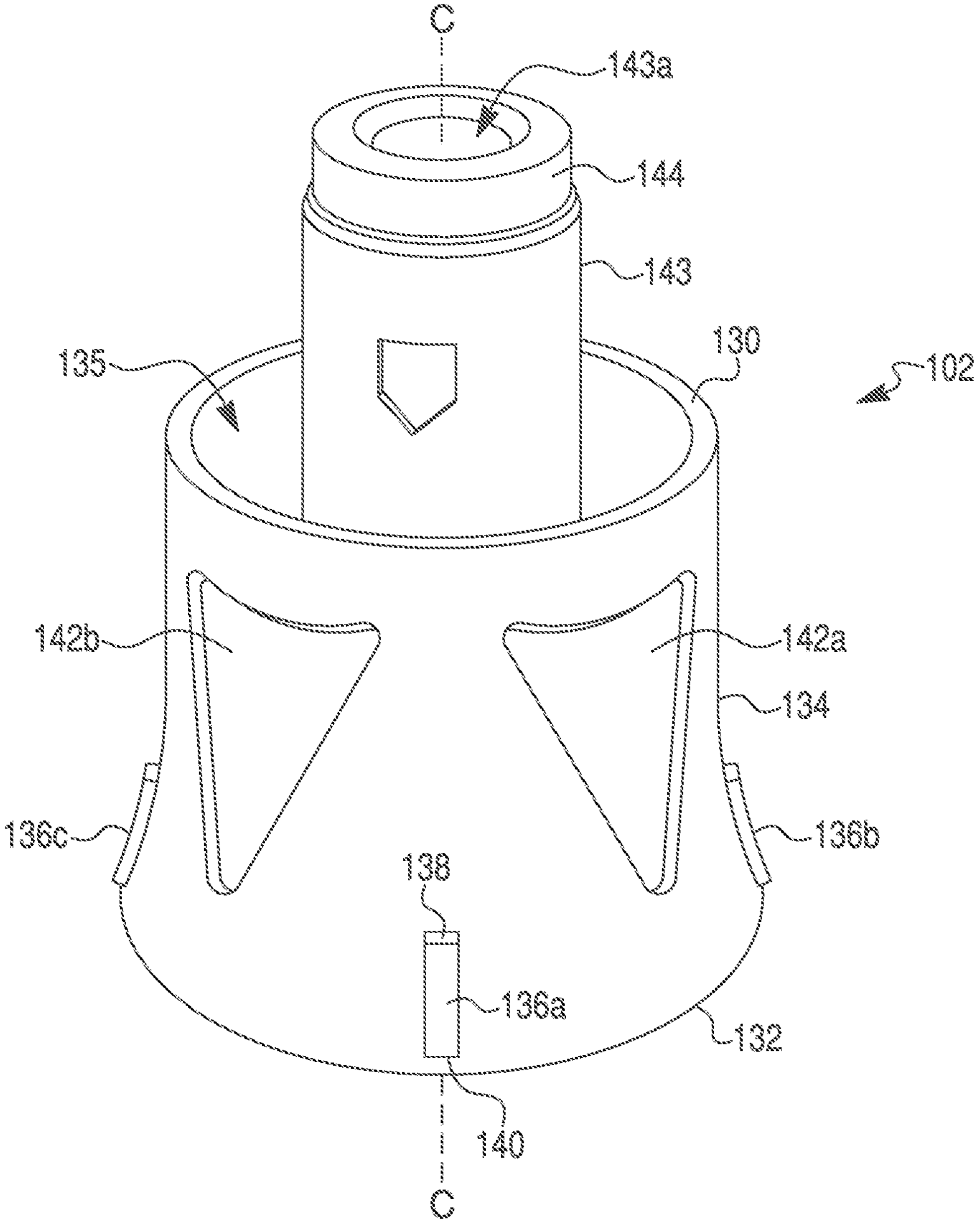
FIG. 3A provides a perspective view of an exemplary cap of a therapeutic agent delivery device of the present disclosure, such as the one depicted in FIG. 1A.
Figure 3B:
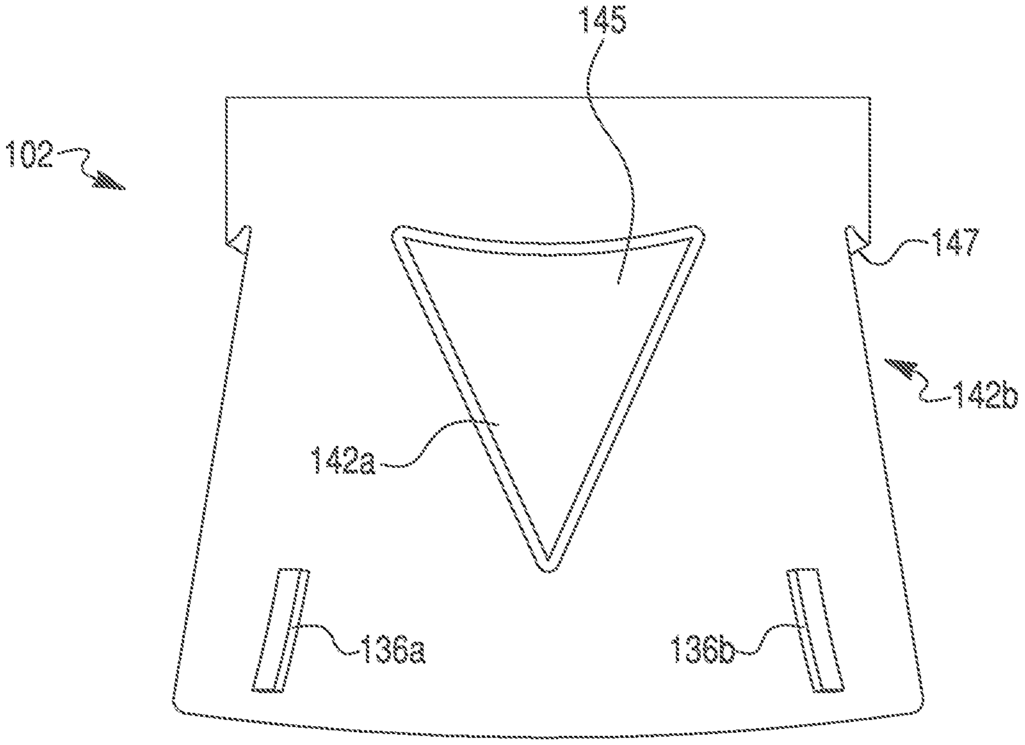
FIG. 3B provides a side view of the cap depicted in FIG. 3A.
Figure 4A:
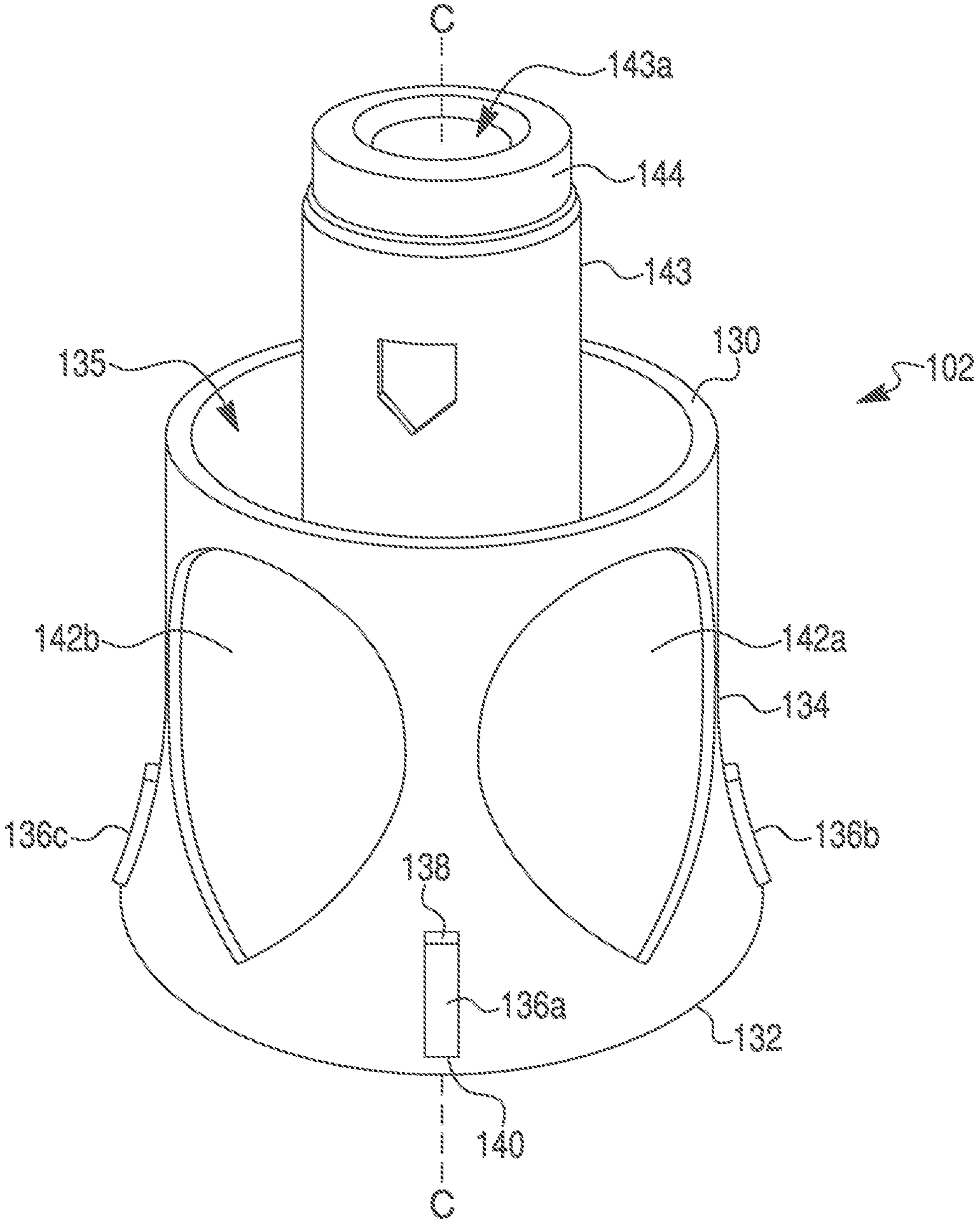
FIG. 4A provides a perspective view of an alternative exemplary cap of a therapeutic agent delivery device of the present disclosure, such as the one depicted in FIG. 1A.

As shown in, e.g., FIGS. 3A and 4A, an outer surface of skirt 134 may be curved inward as it extends from proximal end portion 132 to distal end portion 130. Stated differently, the outer surface of skirt 134 may curve radially outward as it extends from distal end portion 130 to proximal end portion 132. In some embodiments, for example, the curve of the outer surface of skirt 134 may include a substantially concave configuration when viewed from a perspective radially outward of cap 102. In other embodiments, the configuration may be substantially convex when viewed from the perspective. The curvature of skirt 134 may be configured to facilitate gripping by a user during handling of cap 102. In still further embodiments, some or all of the outer surface of skirt 134 may be substantially linear when viewed from the perspective. In some embodiments, as shown in, e.g., FIG. 5A, outer skirt 134 may have a crease such that part of outer surface of skirt 134 (e.g., extending to proximal end portion 132), may be angled outward. Such outward angling may also be configured to facilitate gripping by a user during handling of cap 102.

The outer surface of skirt 134 also may include one or more protrusions 136, such as, e.g., protrusions 136*a*-136*d*. Protrusions 136*a*-136*d* may be substantially similar to one another or may include differing configurations. For the sake of brevity, the following description is provided relative to a single protrusion 136 (e.g., protrusions 136*a*). Protrusion 136*a* may include a generally rectangular configuration. As shown in FIGS. 3A, 3B, 4A, 5A, and 5B, a length of protrusion 136*a* may generally be disposed along a direction of longitudinal axis C-C. Those of ordinary skill will understand that protrusion may include any suitable configuration or shape. For example, instead of a rectangular configuration, protrusion 136*a* may include a generally oblong, circular, or triangular configuration. Regardless of configuration, protrusion 136*a* may generally follow the aforementioned curvature of outer surface of skirt 134.

Skirt 134 may include any suitable number of protrusions 136*a*. For example, even though four protrusions 136*a*-136*d* are depicted, those of ordinary skill in the art will understand that skirt 134 may be provided with, e.g., at least or exactly one, at least or exactly two, at least or exactly three, at least or exactly five, at least or exactly six, at least or exactly seven, at least or exactly eight, or more than 8 protrusions. In addition, some embodiments of skirt 134 may not include any protrusions. In those embodiments where skirt 134 is provided with more than one protrusion 136*a*, the protrusions may be spaced from one another by any suitable distance. For example, the protrusions may be equally spaced apart about the outer surface of skirt 134. Protrusion 136*a* may be disposed at any position along a length of skirt 134. For example, protrusion 136*a* may be disposed centrally between distal end portion 130 and proximal end portion 132 (not shown), closer to proximal end portion 132, or closer to distal end portion 130 (not shown). Protrusion 136*a* may include a first end 138 and a second end 140. The first end 138 may be spaced from the central longitudinal axis C-C a first distance and the second end 140 of the protrusion 136 may be spaced from central longitudinal axis C-C by a second distance greater than the first distance.

Cap 102 also may include one or more recesses 142, e.g., recesses 142*a* and 142*b*. Though only two recesses 142 are depicted, cap 102 may include a greater or lesser number of recesses 142. For example, cap 102 may include, e.g., at least or exactly one, at least or exactly three, at least or exactly four, at least or exactly five, at least or exactly six, at least or exactly seven, at least or exactly eight, or more than eight recesses 142. In some embodiments, cap 102 may be provided without any recesses 142. Recesses 142 may extend partially through a thickness of skirt 134. In some embodiments, one or more recesses 142 may extend completely through a thickness of skirt 134.

Recesses 142 may include any suitable configuration. For example, recesses 142 may include an inverted triangular shape (as shown in FIGS. 3A-3D, 5A, and 5B). The inverted triangular recesses 142 may include one or more straight or curved sides, or a combination of straight and curved sides (e.g., to form an arrowhead-like shape). For example, FIGS. 3A-3D, 5A, and 5B illustrate exemplary recesses 142 with a curved side for the side of the recesses 142 closest to distal end portion 130 of cap 102. Specifically, as shown in, e.g., FIG. 3A and FIGS. 5A and 5B, a base side of recess 142*b* may include a concave curvature. The leg sides of recesses 142 may also include curvature, e.g., a convex curvature. Alternately or in addition, recesses 142 may include a tear-drop shape (as shown in FIGS. 4A-4C). The tear-drop shape may include a wider based disposed in a direction closer to distal end portion 130 or closer to proximal end portion 132. In some aspects, recesses 142 may include a substantially equilateral triangular configuration. In other aspects, recesses 142 may include a triangular shape having an isosceles configuration, wherein the legs of the triangular shape may include a substantially equal length that is greater than a length of the base, as shown in, e.g., FIG. 3A. A single cap 102 may also include recesses 142 of different shapes, for example, having alternating triangular or tear-drop shapes. One or more recesses 142 may include a distal width larger than a proximal width. In such embodiments, the narrow proximal width of recesses 142 may be configured to indicate (e.g., point toward) the injection end or direction to a user of device 100. Alternatively, one or more recesses 142 may include a distal width smaller than a proximal width. Alternately or in addition, recesses 142 may include a distinct configuration to indicate a particular therapeutic agent contained within syringe 106, a quantity of the therapeutic agent disposed in syringe 106, a rate of agent delivery from syringe 106, or a combination thereof. For example, a teardrop-shaped recess 142 (e.g., of FIG. 4A) may indicate a specific dosage amount of a selected therapeutic agent, while a triangular recess 142 (e.g., of FIG. 3A or 5A) may indicate a second dosage amount of the same therapeutic agent. Alternately, a teardrop-shaped recess 142 may indicate a specific dosage amount of a selected therapeutic agent, while a triangular recess 142 may indicate a second dosage amount of a second therapeutic agent, different from the selected therapeutic agent. Indications may also be provided via colors, textures, or any distinguishing features known to one of ordinary skill in the art. In addition, as shown in FIGS. 3C and 4B, a depth to which a recess 142 may extend into the thickness of skirt 134 may be constant or may vary across a width and/or length of the recess 142. In some embodiments, each of recesses 142 may include a similar configuration. In other embodiments, one or more recesses 142 may differ from other recesses 142 provided on skirt 134. Each recess 142 may include a surface 145 that may either follow or deviate from the above-described curvature of skirt 134. Surface 145 of recess 142 may be provided with any suitable texturing and/or surface treatment to increase gripping during handling of cap 102.

Figure 3D:
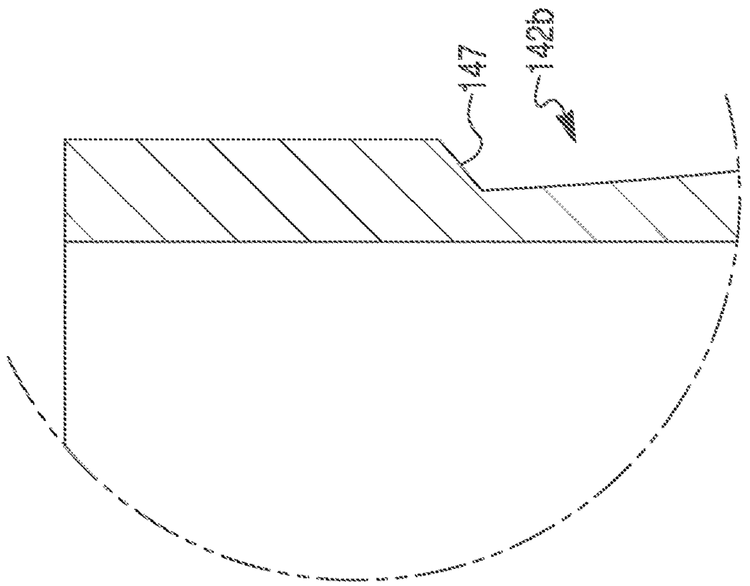
FIG. 3D provides a close-up view of a recess depicted in FIG. 3C.
Figure 3C:
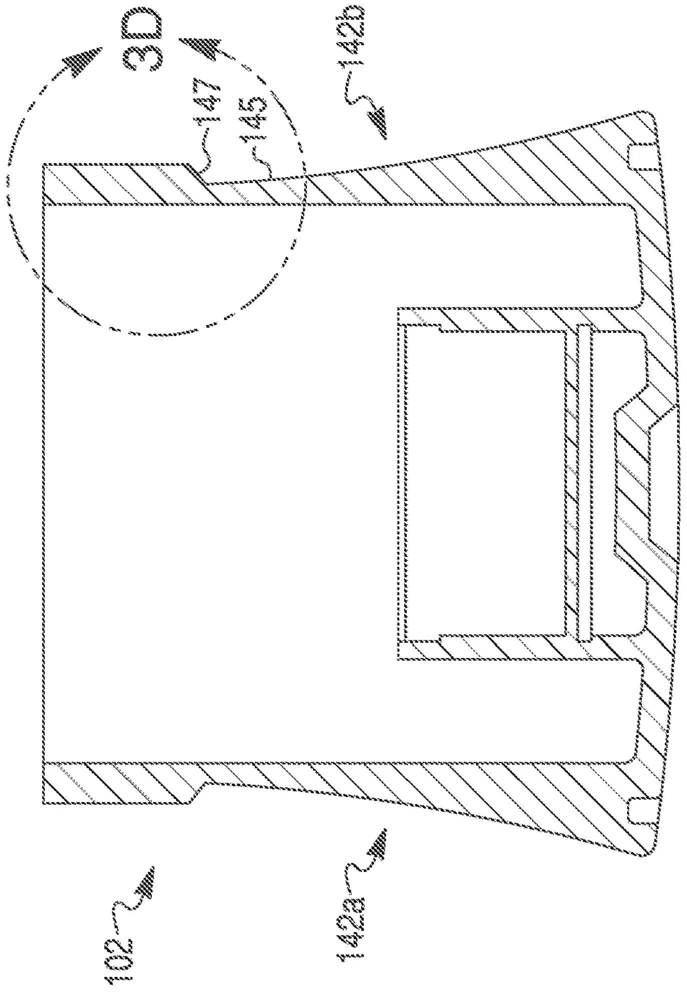
FIG. 3C provides a cross-sectional view of the cap depicted in FIG. 3A.
Figure 3E:
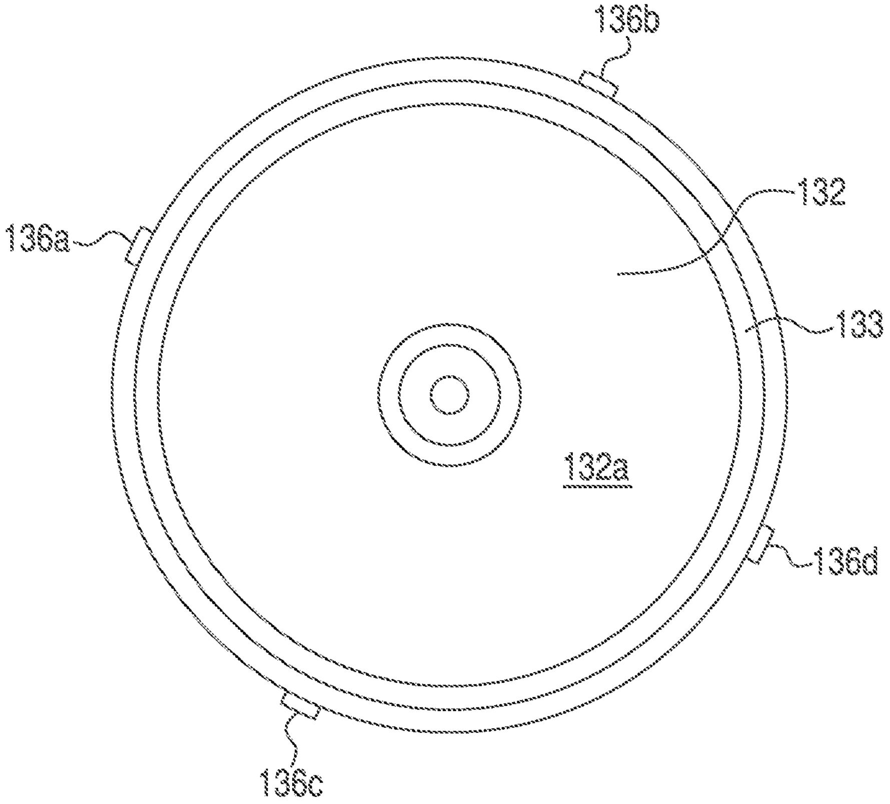
FIG. 3E provides a top view of the cap depicted in FIG. 3A.
Figure 4B:
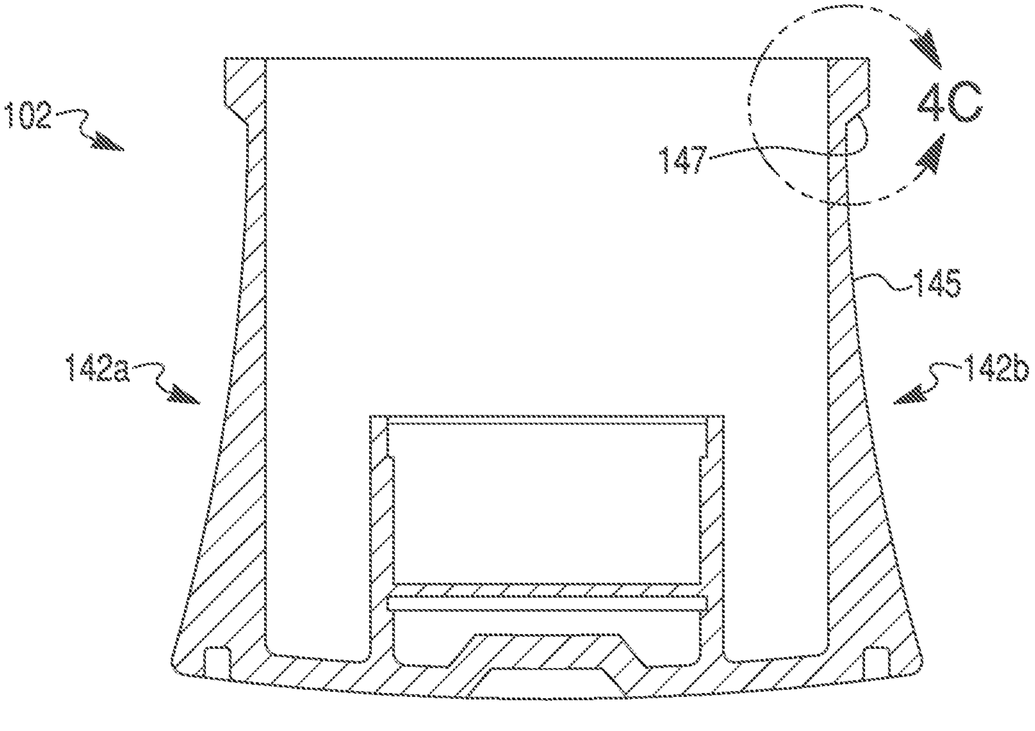
FIG. 4B provides a cross-sectional view of the cap depicted in FIG. 4A.
Figure 4C:
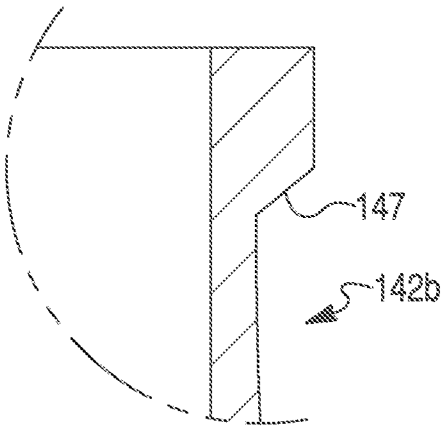
FIG. 4C provides a close-up view of a recess depicted in FIG. 4B.

As shown in FIGS. 3B-3D, 4B, 4C, 5A, and 5B, each recess 142 may further include a beveled surface 147 defining the depth of recess 142. Surface 147 may include a straight surface (as shown in FIGS. 3C, 3D, 4B, 4C, 5A, and 5B), where surface 147 is depicted as a straight discontinuity of the surface of skirt 134. Alternately, surface 147 may include a curved discontinuity in the surface of skirt 134. One or more edges of surface 147 may also be curved or straight, where the shape of recesses 142 may be determined by the edges of surface 147. Furthermore, surface 147 may define the depth of recess 142. For example, surface 147 may define the depth of recess 142 by way of an angular slope (as shown in FIGS. 3D and 4C), where surface 147 may include a surface that is at an angle relative to longitudinal axis C-C and/or relative to the surface of skirt 134. The angular slope may include a perpendicular angle, for example, where surface 147 may be perpendicular to the surface of skirt 134 or define a concave lip in the surface of skirt 134. Recesses 142 may include surface 147 at one portion of recess 142, while other portions of recesses 142 gradually form or become flush with skirt 134 (as shown in FIGS. 3B-3D and 4B). In such embodiments, recess 142 may extend into skirt 134 at varying depths. Alternately, recesses 142 may include surface 147 around the entire perimeter of recess 142. In other words, the depth of recess 142 in the surface of skirt 134 may remain constant such that surface 147 extends into the surface of skirt 134 at every point in the perimeter of recess 142.

As shown in at least FIGS. 3A, 3B, 4A, 4B, and 5A-5C, each of recess 142 may be positioned between adjacent protrusions 136. Those of ordinary skill will understand that recesses 142 may be provided in between only certain pairs of adjacent protrusions 136. That is, recesses 142 may be omitted from in between certain pairs of adjacent protrusions. The number and configuration of recesses 142 may be configured to facilitate gripping by a user during handling of cap 102.

Figure 5A:
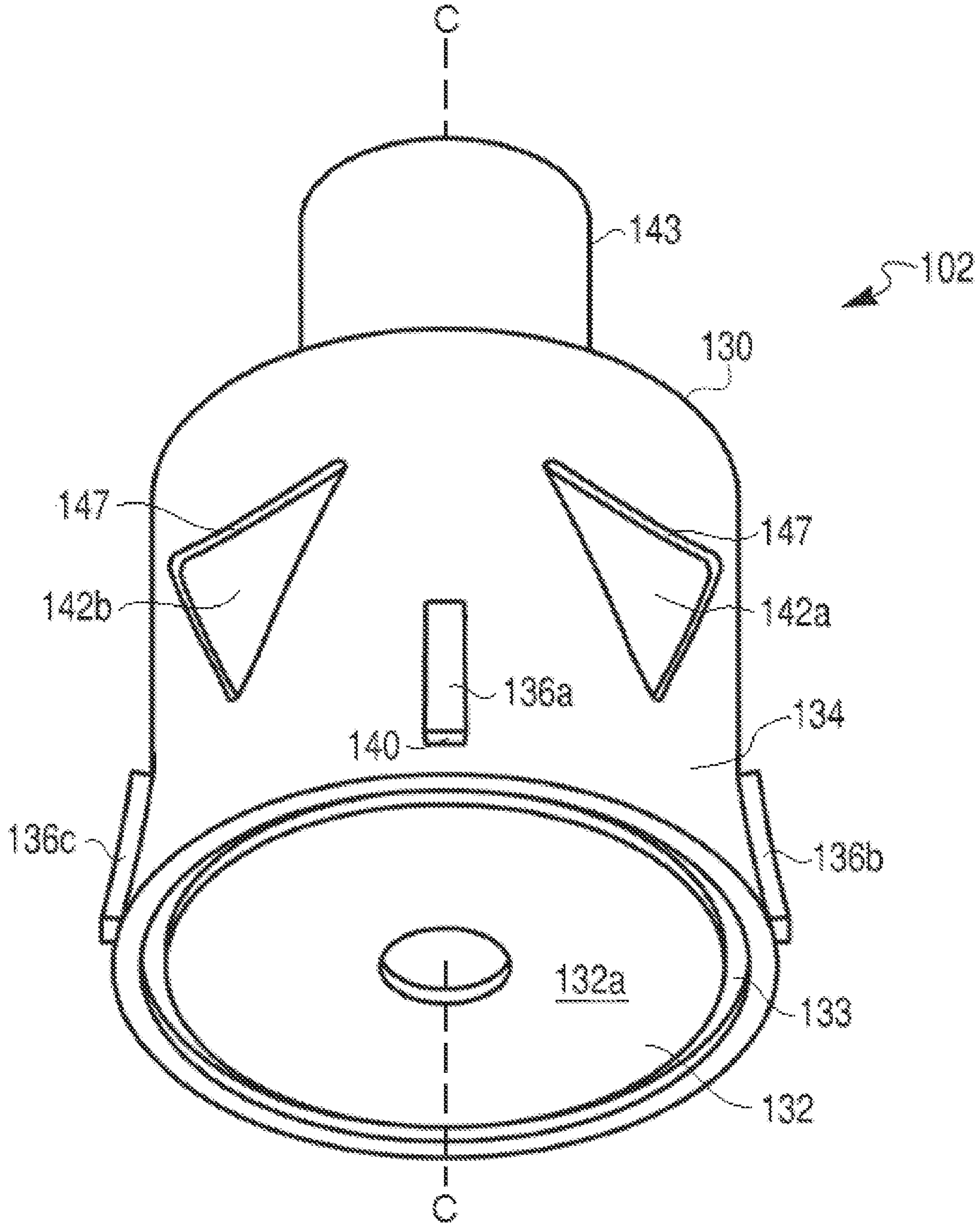
FIG. 5A provides a perspective view of another alternative exemplary cap of a therapeutic agent delivery device of the present disclosure, such as the one depicted in FIG. 1A.
Figure 5B:
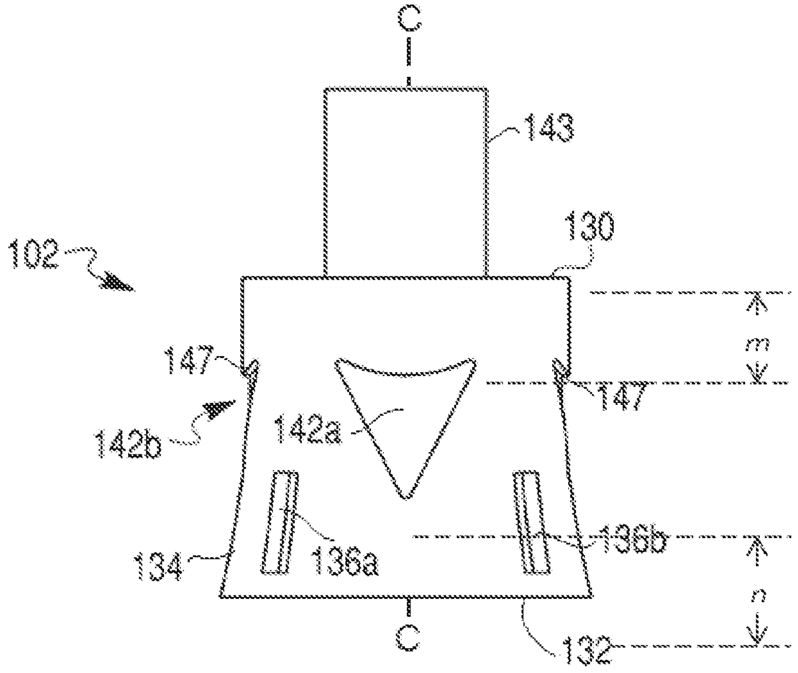
FIG. 5B provides a side view of the cap depicted in FIG. 5A.
Figure 5C:
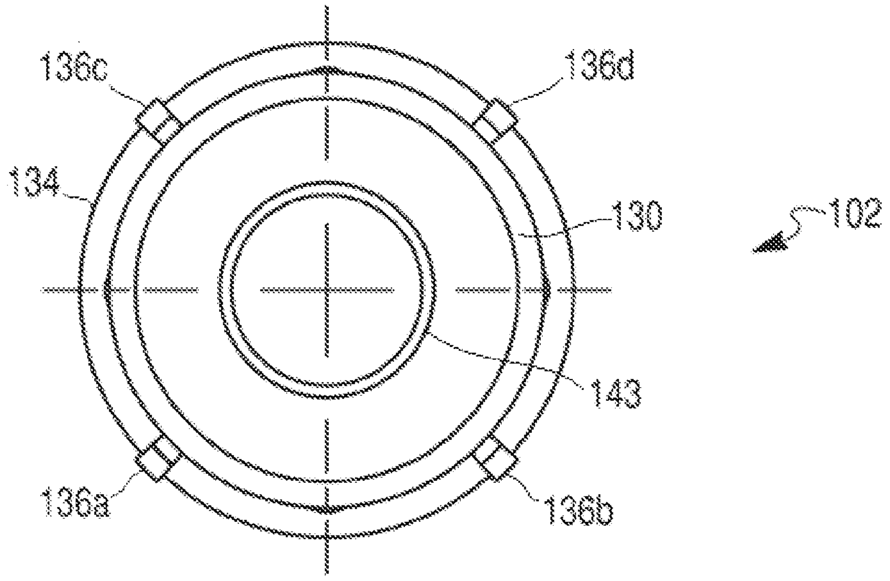
FIG. 5C provides a bottom view of the cap depicted in FIG. 5A.

As shown in FIGS. 3A, 4A, and 5A, for example, each recess 142 may be positioned any suitable distance from distal end portion 130 and proximal end portion 132 of cap 102. For example, as shown in FIG. 5B, a recess 142 may be positioned a distance m from distal end portion 130 and a distance n from proximal end portion 132. Distance m may be measured from, e.g., an end of recess 142 closest to distal end portion 130 to an edge of cap 102 at distal end portion 130, and distance n may likewise be measured from, e.g., an end of recess 142 closest to proximal end portion 132 to an edge of cap 102 at proximal end portion 132. Distance m and distance n may both be any distance allowing recess 142 to fit on and/or within cap 102. In some embodiments, each of distances m and n may be between about 0.5 mm and about 5 mm, such as between about 1 mm and about 4.5 mm, between about 1.5 mm and about 4.5 mm, between about 2 mm and about 4.5 mm, between about 2.5 mm and about 4.5 mm, or between about 3 mm and about 4.5 mm. For example, each of distance m and distance n may be about 0.5 mm, about 1 mm, about 1.5 mm, about 2 mm, about 2.5 mm, about 3 mm, about 3.5 mm, about 4 mm, about 4.5 mm, or about 5 mm, or any other distance. In some embodiments, distance m may be between about 3.1 mm and 3.9 mm, such as about 3.3 mm, 3.35 mm, 3.4 mm, 3.45 mm, 3.5 mm, 3.55 mm, 3.6 mm, 3.65 mm, 3.7 mm, 3.75 mm, 3.8 mm, 3.85 mm, 3.9 mm, or 3.95 mm. In one embodiment, for example, distance m may be about 3.365 mm. In some embodiments, distance n may be between about 3.9 mm and about 4.5 mm, such as about 3.9 mm, about 4 mm, about 4.05 mm, about 4.1 mm, about 4.15 mm, about 4.2 mm, about 4.25 mm, about 4.3 mm, about 4.35 mm, about 4.4 mm, about 4.45 mm, or about 4.5 mm. In one embodiment, for example, distance n may be about 4.262 mm. It is to be understood that these dimensions are exemplary, and one of ordinary skill in the art will understand that many other dimensions and ranges of dimensions are possible.

Figure 5D:
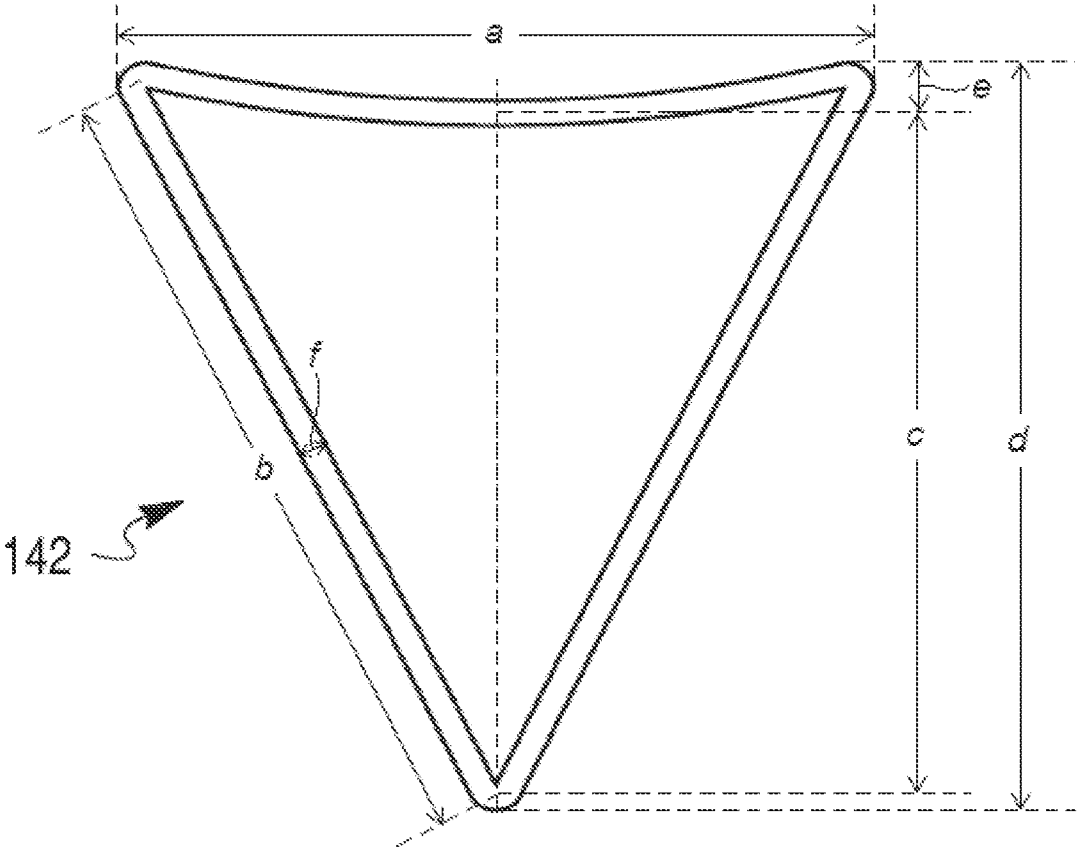
FIG. 5D provides a close-up view of a recess depicted in FIG. 5A, as well as several dimensions of the recess.

Each recess 142 may also have any suitable dimensions (e.g., length, width, height, recess depth) for fitting on cap 102. FIG. 5D depicts an exemplary triangular recess 142 having one curved side and a plurality of dimensions a-f. Table 1 below lists some exemplary measurements of dimensions a-f. It is to be understood that these measurements are approximate and merely exemplary, and many other possible measurements of dimensions a-f (or other dimensions of a recess 142) may be suitable.

TABLE 1

| Dimension | Exemplary measurement range(s) (mm) | Exemplary measurement (mm) |
|---|---|---|
| a | 1-12, 5-10, 6-10, 7-10, 8-10, 9-10 | 9.5325 |
| b | 1-12, 5-10, 6-10, 7-10, 8-10, 9-10 | 9.1394 |
| c | 1-10, 3-9, 4-8, 5-8, 6-8, 7-8 | 7.4116 |
| d | 1-11, 3-10, 3-9, 4-8, 5-8, 6-8, 7-8 | 8.1015 |
| e | 0.1-5, 0.1-3, 0.1-1, 0.1-0.5 | 0.3558 |
| f | 0.1-1, 0.1-0.5, 0.1-0.4, 0.2-0.4, 0.3-0.4 | 0.3811 |

In some embodiments, a color of cap 102 may be coordinated with a color of ledge 114. For example, a color of protrusions 136 may be coordinated with a color of ledge 114. Similarly, a color of recesses 142 may be coordinated with a color of ledge 114. Though it is contemplated that the described coordination may include matching colors, those of ordinary skill will understand that other color coordination schemes are within the scope of the present disclosure. The coordination between one or more colors of cap 102 and ledge 114 (or housing 104) may assist a user in engaging the cap 102 with its respective housing.

With renewed reference now to FIGS. 1A-1C and 2A-2B, ledge 114 may be configured to prevent or otherwise inhibit rolling of housing 104 when, e.g., housing 104 is on a flat surface. For example, when housing 104 is on a surface such that axis X-X is substantially parallel to the surface, ledge 114 may frictionally engage the surface to prevent or otherwise inhibit housing 104 from rolling on the surface. Moreover, ledge 114 may be configured to stop or otherwise slow a rotational speed of a housing 104 already rolling on the surface. To provide improved anti-roll performance, all or some portion of ledge 114 may include a tacky, e.g., a rubber coating, to increase friction.

Similarly, protrusions 136 may be configured to prevent or otherwise inhibit rolling of cap 102 when, e.g., cap 102 is on a flat surface. For example, when cap 102 is on a surface such that axis C-C is substantially parallel to the surface, or not substantially perpendicular to the surface, one or more protrusions 136 may frictionally engage the surface to prevent or otherwise inhibit cap 102 from rolling on the surface. Moreover, one or more of protrusion 136 may be configured to stop or otherwise slow a rotational speed of a cap 102 already rolling on the surface. To provide improved anti-roll performance, all or some portion of protrusions 136 may include a tacky, e.g., a rubber coating, to increase friction.

As alluded to above, cap 102 may include a proximal end portion 132 having a diameter greater than a diameter of distal end portion 130. As a result, when cap 102 is engaged with housing 104, and delivery device 100 is on a surface, proximal end 101*b* of housing 104 may be elevated off of the surface, such that axis X-X forms an angle with the surface. As a result of such elevation, all or a portion of ledge 114 may be prevented from contacting the surface. In such instances, protrusions 136 serve to frictionally engage the surface to prevent or otherwise inhibit delivery device 100 from rolling on the surface. Moreover, protrusion 136 may be configured to stop or otherwise slow a rotational speed of a delivery device 100 already rolling on the surface.

In some embodiments, devices according to the present disclosure may be used for packaging and/or delivery of a therapeutic agent for treating a patient. For example, in some embodiments, devices according to the present disclosure may be used for packaging and/or delivery of therapeutic agents for the treatment, management, or prevention of, e.g., arthritis, asthmas, chronic pain (e.g., chronic lower back pain), allergic reactions, diseases, and conditions (e.g., eosinophilic esophagitis), dermatitis, muscle-wasting diseases, hypercholesterolemia, abnormal LDL cholesterol levels, cardiovascular events, bacterial or viral infections, or other conditions, symptoms, or diseases. In some embodiments, therapeutic agents according to the present disclosure may include small molecules (e.g., molecules having a molecular weight of 900 Da or less) or large molecules (e.g., molecules having a molecular weight of over 900 Da). In some embodiments, therapeutic agents according to the present disclosure may include macromolecules, such as proteins, antibodies, or parts of antibodies having a molecular weight of over 30 kDa. For example, therapeutic agents for use with devices of the present disclosure may include, e.g., dupilumab, alirocumab, evolocumab, trevogrumab, evinacumab, sarilumab, or fasinumab. In some embodiments, therapeutic agents according to the present disclosure may include PCSK9 inhibitors, interleukin-4 receptor inhibitors, interleukin-5 receptor inhibitors, or interleukin-13 receptor inhibitors. In some embodiments, devices according to the present disclosure may be used for delivery of therapeutic agents to patients in a population that might benefit from anti-roll features, such as geriatric patients, patients with rheumatoid arthritis, pediatric patients, and/or patients with physical or mental disabilities.

The description above and examples are illustrative, and are not intended to be restrictive. One of ordinary skill in the art may make numerous modifications and/or changes without departing from the general scope of the invention. For example, and as has been described, the above-described embodiments (and/or aspects thereof) may be used in combination with each other. Additionally, portions of the above-described embodiments may be removed without departing from the scope of the invention. In addition, modifications may be made to adapt a particular situation or aspect to the teachings of the various embodiments without departing from their scope. Many other embodiments will also be apparent to those of skill in the art upon reviewing the above description.

Additionally, while a number of objects and advantages of the embodiments disclosed herein (and variations thereof) are described, not necessarily all such objects or advantages may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

What is claimed is:

1. A therapeutic agent delivery device, comprising:

a housing including a distal end, a proximal end, and a lumen extending between the distal end and the proximal end, wherein an outer surface of the housing includes a first opening for visualization into the housing; and a cap configured to engage the proximal end of the housing, wherein the cap includes a central longitudinal axis, a distal end having a first cross-sectional dimension, a proximal end having a second cross-sectional dimension larger than the first cross-sectional dimension, wherein the cap further includes:

a first radially outermost surface and a second surface disposed radially offset from the first radially outermost surface, the second surface defining surfaces of a plurality of recesses extending partially into a thickness of the cap, wherein each recess of the plurality of recesses is enclosed by a continuous ledge surrounding the second surface, wherein the continuous ledge defines a depth of each recess of the plurality of recesses, each recess of the plurality of recesses including a distal width larger than a proximal width, the continuous ledge forming an acute angle at the proximal width, and wherein a portion of each recess of the plurality of recesses is arrow-shaped; and a plurality of protrusions located adjacent the proximal end of the cap, wherein each protrusion of the plurality of protrusions has a width and a length, wherein the length of each protrusion of the plurality of protrusions is greater than the width of each protrusion, the length of each protrusion of the plurality of protrusions extending along the first radially outermost surface of the cap from the proximal end of the cap towards the distal end of the cap, wherein each recess of the plurality of recesses is located between adjacent protrusions, and wherein the plurality of protrusions are located closer to the proximal end of the cap than the plurality of recesses, and wherein the plurality of recesses are located closer to the distal end of the cap than the plurality of protrusions.

2. The therapeutic agent delivery device of claim 1, wherein a width of the first opening is about 7.5 mm and a length of the first opening is about 31.9 mm.

3. The therapeutic agent delivery device of claim 1, wherein the therapeutic agent delivery device contains dupilumab.

4. The therapeutic agent delivery device of claim 1, wherein the lumen is configured to receive a medicament container therein.

5. The therapeutic agent delivery device of claim 4, wherein the medicament container includes a syringe having a volume of a therapeutic agent, and wherein the first opening is configured to permit visualization of the volume of the therapeutic agent.

6. The therapeutic agent delivery device of claim 1, wherein the housing further includes a second opening disposed diametrically opposite to the first opening.

7. The therapeutic agent delivery device of claim 6, wherein the second opening is shaped as a circle, rectangle, triangle, pentagon, octagon, or oval.

8. The therapeutic agent delivery device of claim 1, wherein each recess of the plurality of recesses includes a plurality of sides, wherein the plurality of sides include a straight side, a curved side, or a combination of both.

9. The therapeutic agent delivery device of claim 1, wherein the proximal end of the housing is an injection end and the proximal width of each recess of the plurality of recesses is configured to indicate the injection end to a user of the therapeutic agent delivery device.

10. The therapeutic agent delivery device of claim 1, wherein the second surface of each recess of the plurality of recesses is positioned closer to the central longitudinal axis of the cap than the first radially outermost surface.

11. The therapeutic agent delivery device of claim 1, wherein the proximal end of the cap includes a substantially flat configuration.

12. The therapeutic agent delivery device of claim 1, wherein the first opening includes a surface defining the depth of the first opening.

13. The therapeutic agent delivery device of claim 12, wherein the surface of the first opening is flush with the outer surface of the housing.

14. The therapeutic agent delivery device of claim 1, wherein the plurality of protrusions includes at least four protrusions.

15. The therapeutic agent delivery device of claim 1, wherein a diameter of the distal end of the cap is substantially equal to an outer diameter of the housing.

16. The therapeutic agent delivery device of claim 1, wherein each protrusion of the plurality of protrusions has a rectangular shape.

17. The therapeutic agent delivery device of claim 1, wherein each protrusion of the plurality of protrusions is equally spaced apart about the first radially outermost surface of the cap.

18. The therapeutic agent delivery device of claim 1, wherein each protrusion of the plurality of protrusions has a rectangular shape, and wherein each protrusion of the plurality of protrusions is equally spaced apart about the first radially outermost surface of the cap.

19. The therapeutic agent delivery device of claim 1, wherein each protrusion of the plurality of protrusions has a rectangular shape, wherein each protrusion of the plurality of protrusions is equally spaced apart about the first radially outermost surface of the cap, and wherein a diameter of the distal end of the cap is substantially equal to an outer diameter of the housing.

20. The therapeutic agent delivery device of claim 1, wherein positioning of the plurality of protrusions is configured to facilitate gripping of the cap.

* * * * *